US010792311B2

(12) United States Patent
Cheng et al.

(10) Patent No.: US 10,792,311 B2
(45) Date of Patent: *Oct. 6, 2020

(54) STIMULATION OF OVARIAN FOLLICLE DEVELOPMENT AND OOCYTE MATURATION

(71) Applicant: The Board of Trustees of the Leland Stanford Junior University, Stanford, CA (US)

(72) Inventors: Yuan Cheng, San Diego, CA (US); Aaron J. W. Hsueh, Stanford, CA (US); Yorino Sato, Kawasaki (JP)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 131 days.

This patent is subject to a terminal disclaimer.

(21) Appl. No.: 15/978,947

(22) Filed: May 14, 2018

(65) Prior Publication Data

US 2018/0256649 A1    Sep. 13, 2018

Related U.S. Application Data

(63) Continuation of application No. 14/364,286, filed as application No. PCT/US2012/069856 on Dec. 14, 2012, now Pat. No. 10,010,565.

(60) Provisional application No. 61/570,746, filed on Dec. 14, 2011.

(51) Int. Cl.
| | | |
|---|---|---|
| *A61K 35/54* | (2015.01) | |
| *A61K 38/16* | (2006.01) | |
| *A61K 38/22* | (2006.01) | |
| *A61K 38/24* | (2006.01) | |
| *C12N 5/075* | (2010.01) | |
| *A61K 38/17* | (2006.01) | |
| *A61K 39/395* | (2006.01) | |

(52) U.S. Cl.
CPC ............ *A61K 35/54* (2013.01); *A61K 38/16* (2013.01); *A61K 38/1703* (2013.01); *A61K 38/22* (2013.01); *A61K 38/2242* (2013.01); *A61K 38/24* (2013.01); *A61K 39/39533* (2013.01); *C12N 5/0609* (2013.01); *C12N 2501/30* (2013.01); *C12N 2501/415* (2013.01); *C12N 2501/998* (2013.01); *C12N 2517/10* (2013.01)

(58) Field of Classification Search
None
See application file for complete search history.

(56) References Cited

U.S. PATENT DOCUMENTS

| | | | |
|---|---|---|---|
| 6,737,272 B2 | 5/2004 | Kuo et al. | |
| 10,010,565 B2 * | 7/2018 | Cheng | ................... A61K 35/54 |
| 2010/0071078 A1 * | 3/2010 | Niehrs | ................ C12Q 1/6883 |
| | | | 800/3 |
| 2010/0191040 A1 | 7/2010 | Hsueh et al. | |

FOREIGN PATENT DOCUMENTS

| | | |
|---|---|---|
| JP | 2007/535303 A | 12/2007 |
| WO | 2000/032222 A1 | 6/2000 |
| WO | 2005/054449 A1 | 6/2005 |

OTHER PUBLICATIONS

McGee et al., Endocrinology. Jun. 1997;138(6):2417-24.*
Zhang et al., Science. Oct. 15, 2010;330(6002):366-9.*
Gook et al., Human Reproduction, vol. 16, Issue 3, Mar. 2001, pp. 417-422.*
Theofanakis et al., "Human Chorionic Gonadotropin: The Pregnancy Hormone and More", Int J Mol Sci., May 14, 2017, pp. 1-8, 18(5), MDPI, Basel, Switzerland.
Gutkowska et al., "Hormonal regulation of natriuretic peptide system during induced ovarian follicular development in the rat", Biol Reprod., Jul. 1999, pp. 162-170, 61(1), Oxford University Press, Oxford, United Kingdom.
Knight et al., "R-spondins: novel matricellular regulators of the skeleton", Matrix Bioi., Jul. 2014, pp. 157-161, vol. 37, http://dx.doi.org/10.1016/j.matbio.2014.06.003, Elsevier, New York City, NY.
Yoon et al., "Cellular signaling and biological functions of R-spondins", Cell Signal, Feb. 2012, pp. 369-377, vol. 24, Issue 2, Elsevier, New York City, NY.
Jin et al., "The R-spondin family of proteins: emerging regulators of WNT signaling", Int J Biochem Cell Bioi., Dec. 2012, pp. 2278-2287, vol. 44, Issue 12, Elsevier, New York City, NY.
McGee et al "Preantral ovarian follicles in serum-free culture: suppression of apoptosis after activation of the cyclic guanosine 3',5'-monophosphate pathway and stimulation of growth and differentiation by follicle-stimulating hormone" Endocrinology, Jun. 1, 1997, pp. 2417-2424, vol. 138, No. 6, Endocrine Society, Washington, DC.
Chassot et al., "Activation of beta-catenin signaling by Rspo1 controls differentiation of the mammalian ovary", Hum. Mol. Genet., May 1, 2008, pp. 1264-1277, vol. 17, Issue 9, Oxford University Press, Oxford, United Kingdom.
Fan et al., "Beta-catenin (CTNNB1) promotes preovulatory follicular development but represses LH-mediated ovulation and luteinization.", Mol. Endocrinol., Aug. 1, 2010, pp. 1529-1542, vol. 24, Issue 8, Oxford University Press, Oxford, United Kingdom.

(Continued)

*Primary Examiner* — Michael Szperka
(74) *Attorney, Agent, or Firm* — Pamela J. Sherwood; Bozicevic, Field & Francis LLP

(57) ABSTRACT

Methods are provided for stimulating ovarian preantral and antral follicles in a mammal.

5 Claims, 15 Drawing Sheets

(56) References Cited

OTHER PUBLICATIONS

Gutkowska et al., "Hormonal regulation of natriuretic peptide system during induced ovarian follicular development in the rat", Bioi. Reprod., Jul. 1, 1999, pp. 162-170, vol. 61, Issue 1, Oxford University Press, Oxford, United Kingdom.

Harwood et al., "Members of the WNT signaling pathways are widely expressed in mouse ovaries, oocytes, and cleavage stage embryos", Dev. Dyn., Apr. 2008, pp. 1099-1111, vol. 237, Issue 4, Wiley, Hoboken, NJ.

Jankowski et al., "C-type natriuretic peptide and the guanylyl cyclase receptors in the rat ovary are modulated by the estrous cycle", Bioi. Reprod., Jan. 1, 1997, pp. 59-66, vol. 56, Issue 1, Oxford University Press, Oxford, United Kingdom.

Kawamura et al., "Ovarian brain-derived neurotrophic factor (BDNF) promotes the development of oocytes into preimplantation embryos", Proc. Natl. Acad. Sci. USA., Jun. 28, 2005, pp. 9206-9211, 102 (26), National Academy of Sciences, Washington, DC.

Kim et al., "R-Spondin family members regulate the Wnt pathway by a common mechanism", Mol. Bioi. Cell., Jun. 1, 2008, pp. 2349-2680, vol. 19, No. 6, The American Society for Cell Biology, Bethesda, MD.

Kiyosu et al., "NPPC/NPR2 signaling is essential for oocyte meiotic arrest and cumulus oophorus formation during follicular development in the mouse ovary", Reproduction, Aug. 1, 2012, pp. 187-193, 144(2), Society for Reproduction and Fertility, Middlesex, United Kingdom.

Koller et al., "Selective activation of the B natriuretic peptide receptor by C-type natriuretic peptide (CNP).", Science, Apr. 5, 1991, pp. 120-123, vol. 252, Issue 5002, American Association for the Advancement of Science, Washington, D.C.

Li et al., "Activation of dormant ovarian follicles to generate mature eggs", Proc. Natl. Acad. Sci. USA, Jun. 1, 2010, pp. 10280-10284, National Academy of Sciences, Washington, DC.

Mcgee et al., "Follicle-stimulating hormone enhances the development of preantral follicles in juvenile rats", Bioi. Reprod., Nov. 1, 1997, pp. 990-998, vol. 57, Issue 5, Oxford University Press, Oxford, United Kingdom.

Parma et al., "R-spondin1 is essential in sex determination, skin differentiation and malignancy", Nat. Genet., Nov. 2006, pp. 1304-1309, vol. 38, No. 11, Macmillan Publishers Limited, Basingstoke, United Kingdom.

Sato et al., "C-type natriuretic peptide stimulates ovarian follicle development", Mol. Endocrinol., Jul. 1, 2012, pp. 1158-1166, vol. 26, Issue 7, Oxford University Press, Oxford, United Kingdom.

Sudoh et al., "C-type natriuretic peptide (CNP): a new member of natriuretic peptide family identified in porcine brain", Biochem. Biophys. Res. Commun., Apr. 30, 1990, pp. 863-870, vol. 168, Issue 2, Elsevier, New York City, NY.

Tarlatzis et al., "Clinical management of low ovarian response to stimulation for IVF: a systematic review", Hum. Reprod. Update, Jan. 1, 2003, pp. 61-76, vol. 9, Issue 1, Oxford University Press, Oxford, United Kingdom.

Tomizuka et al., "R-spondin1 plays an essential role in ovarian development through positively regulating Wnt-4 signaling", Hum. Mol. Genet., May 1, 2008, pp. 1278-1291, vol. 17, Issue 9, Oxford University Press, Oxford, United Kingdom.

Zhang et al., "Granulosa cell ligand NPPC and its receptor NPR2 maintain meiotic arrest in mouse oocytes", Science Oct. 15, 2010, pp. 366-339, vol. 330, Issue 6002, American Association for the Advancement of Science, Washington, D.C.

\* cited by examiner

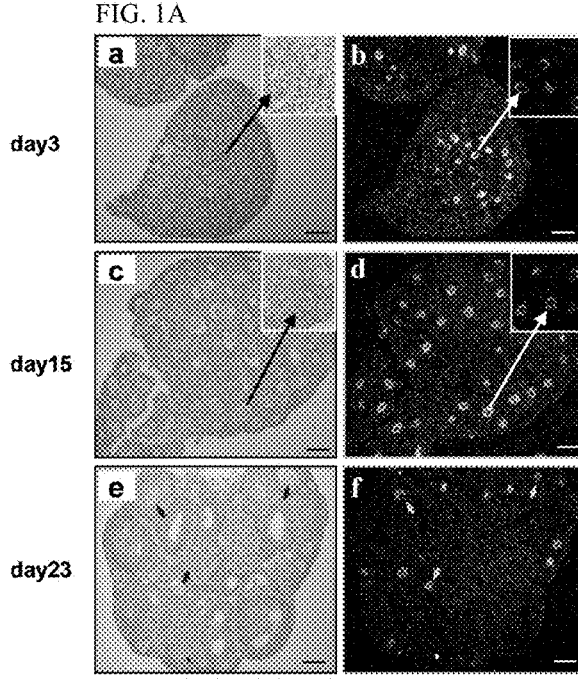
FIG. 1A
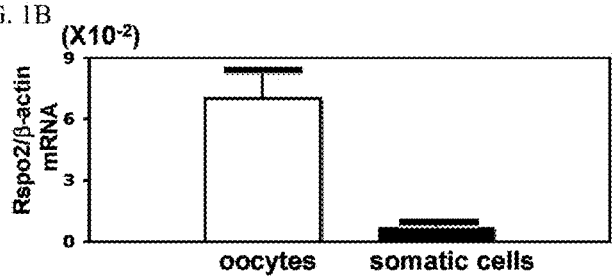
FIG. 1B
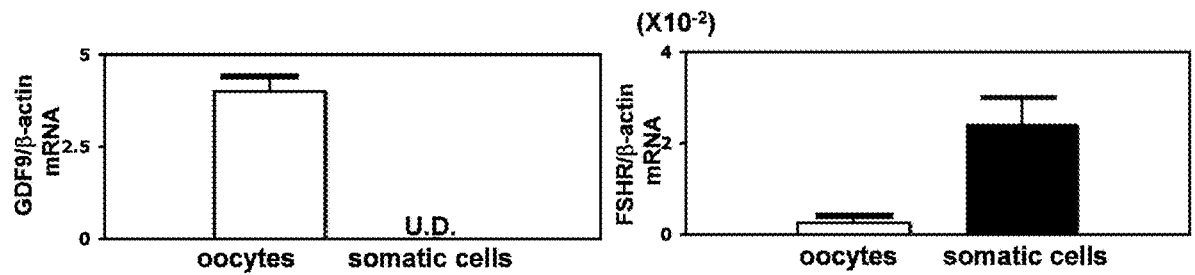

STIMULATION OF OVARIAN FOLLICLE DEVELOPMENT AND OOCYTE MATURATION

CROSS REFERENCE

This application claims benefit and is a Continuation of application Ser. No. 14/364,286 filed Jun. 10, 2014, which is a 371 application and claims the benefit of PCT Application No. PCT/US2012/069856, filed Dec. 14, 2012, which claims benefit of U.S. Provisional Patent Application No. 61/570,746, filed Dec. 14, 2011, which applications are incorporated herein by reference in their entirety.

BACKGROUND OF THE INVENTION

The growth and maturation of mammalian germ cells is intricately controlled by hormones; including gonadotropins secreted by the anterior pituitary; and local paracrine factors. The majority of the oocytes within the adult human ovary are maintained in prolonged stage of first meiotic prophase; enveloped by surrounding follicular somatic cells. Periodically, a group of primordial follicles enters a stage of follicular growth. During this time, the oocyte undergoes a large increase in volume, and the number of follicular granulosa cells increase. The maturing oocyte synthesizes paracrine factors that allow the follicle cells to proliferate, and the follicle cells secrete growth and differentiation factors (for example TGF-$\beta$2, VEGF, leptin, and FGF2) that enhance angiogenesis and allow the oocyte to grow. After progressing to a certain stage, oocytes and their follicles die, unless they are exposed to gonadotropic hormones that prevent somatic cell apoptosis.

Mammalian ovaries consist of follicles as basic functional units. The total number of ovarian follicles is determined early in life, and the depletion of this pool leads to reproductive senescence. Each follicle develops to either ovulate or, more likely, to undergo degeneration. Individual follicles consist of an innermost oocyte, surrounding granulosa cells, and outer layers of thecal cells. The fate of each follicle is controlled by endocrine as well as paracrine factors. The follicles develop through primordial, primary, and secondary stages before acquiring an antral cavity. At the antral stage a few follicles, under the cyclic gonadotropin stimulation that occurs after puberty, reach the preovulatory stage and become a major source of the cyclic secretion of ovarian estrogens in women of reproductive age. In response to preovulatory gonadotropin surges during each reproductive cycle, the dominant Graafian follicle ovulates to release the mature oocyte for fertilization, whereas the remaining theca and granulosa cells undergo transformation to become the corpus luteum.

Once entering the growing pool, ovarian follicles continue to progress into primary, secondary, and early antral stages with minimal loss. Although FSH treatment is widely used to generate preovulatory follicles in infertile patients mainly by suppressing the apoptosis of early antral follicles, some patients are low responders to FSH treatment because their ovaries contain few early antral follicles as reflected by their elevated serum FSH and lower AMH levels on day 3 of the menstrual cycle.

Throughout the reproductive life, primordial follicles undergo initial recruitment to enter the growing pool of primary follicles. In the human ovary, greater than 120 days are required for the primary follicles to reach the secondary follicle stage, whereas 71 days are needed to grow from the secondary to the early antral stage. Once initiated to enter the growing pool, ovarian follicles progress to reach the antral stage and minimal follicle loss was found until the early antral stage. During cyclic recruitment, increases in circulating FSH allow a cohort of antral follicles to escape apoptotic demise. Among this cohort, a leading follicle emerges as dominant by secreting high levels of estrogens and inhibins to suppress pituitary FSH release. The result is a negative selection of the remaining cohort, leading to its ultimate demise. Concomitantly, increases in local growth factors and vasculature allow a positive selection of the dominant follicle, thus ensuring its final growth and eventual ovulation and luteinization. After cyclic recruitment, it takes only 2 weeks for an antral follicle to become a dominant Graafian follicle. The overall development of human follicles from primordial to preovulatory stages require more than six months.

The development of follicles from the smallest primordial and primary follicles to the largest preovulatory follicles requires different stage-dependent stimulatory and survival factors. FSH, activin, nerve growth factor, and GDF-9 are important for the growth and differentiation of primary and/or secondary follicles. The growth of antral and preovulatory follicles is dependent on gonadotropin stimulation, and FSH is a major survival factor to rescue early antral follicles from apoptotic demise during cyclic recruitment. Treatment with FSHctp (a long-acting FSH agonist) has resulted in increased ovarian weight and follicle development. Thus, the development of follicles can be divided into gonadotropin-dependent and gonadotropin-responsive stages.

Methods of efficiently maturing ovarian follicles from primary through secondary, antral, and preovulatory stages is of great interest, including methods for in vitro follicle maturation. The present invention addresses this issue.

Publications

Harwood et al. (2008) Dev Dyn 237:1099-1111, Members of the WNT signaling pathways are widely expressed in mouse ovaries, oocytes, and cleavage stage embryos. Fan et al. (2010) Mol Endocrinol 24:1529-1542, Beta-catenin (CTNNB1) promotes preovulatory follicular development but represses LH-mediated ovulation and luteinization. Kim et al. (2008) Mol Biol Cell 19:2588-2596, R-Spondin family members regulate the Wnt pathway by a common mechanism. McGee et al. (1997) Biol Reprod 57:990-998, Follicle-stimulating hormone enhances the development of preantral follicles in juvenile rats. Tarlatzis et al. (2003) Hum Reprod Update 9:61-76, Clinical management of low ovarian response to stimulation for IVF: a systematic review. Chassot et al. (2008) Hum Mol Genet 17:1264-1277, Activation of beta-catenin signaling by Rspo1 controls differentiation of the mammalian ovary. Tomizuka et al. (2008) Hum Mol Genet 17:1278-1291, R-spondin1 plays an essential role in ovarian development through positively regulating Wnt-4 signaling. Parma et al. (2006) Nat Genet 38:1304-1309 R-spondin1 is essential in sex determination, skin differentiation and malignancy.

Sudoh et al. (1990) Biochem Biophys Res Commun 168:863-870, C-type natriuretic peptide (CNP): a new member of natriuretic peptide family identified in porcine brain. Koller et al. (1991) Science 252:120-123, Selective activation of the B natriuretic peptide receptor by C-type natriuretic peptide (CNP). Jankowski et al. (1997) Biol Reprod 56:59-66, C-type natriuretic peptide and the guanylyl cyclase receptors in the rat ovary are modulated by the estrous cycle. Gutkowska et al. (1999) Biol Reprod 61:162-

170, Hormonal regulation of natriuretic peptide system during induced ovarian follicular development in the rat. Zhang et al. (2010), Science 330:366-369 Granulosa cell ligand NPPC and its receptor NPR2 maintain meiotic arrest in mouse oocytes. Li et al. (2010) Proc Natl Acad Sci USA 107:10280-10284, Activation of dormant ovarian follicles to generate mature eggs. Kawamura et al. (2005) Proc Natl Acad Sci USA 102:9206-9211, Ovarian brain-derived neurotrophic factor (BDNF) promotes the development of oocytes into preimplantation embryos.

SUMMARY OF THE INVENTION

Methods are provided for promoting the pre-antral development of mammalian ovarian follicles in vitro and in vivo, by contacting a primary follicle with an effective dose of at least one of an R-spondin agonist or a CNP agonist, for a period of time sufficient to stimulate the development of a primary follicle to a secondary or pre-antral follicle.

Methods are also provided for antral follicle stimulation, by contacting a pre-antral follicle with an effective dose of a CNP agonist, for a period of time sufficient to stimulate the development of a pre-antral follicle to an antral follicle. CNP is shown herein to promote the development of secondary/preantral follicles to the early antral stage, thus allowing efficient induction of ovulation by an LH agonist, e.g. by sequential eCG-hCG treatment. In some embodiments CNP can substitute for FSH in the penultimate stage of follicle development to the preovulatory stage, and as such CNP treatment could benefit patients with low responses to the conventional FSH treatment.

In some embodiments of the invention, the exposure is performed in vitro, e.g. in an organ or tissue culture, where at least one ovarian follicle is transiently exposed to an effective dose of at least one of an R-spondin agonist or a CNP agonist. The treated follicle may be utilized in vitro, for example for in vitro fertilization, generation of embryonic stem cells, etc., or may be transplanted to provide for in vivo uses. Transplantation modes of interest include, without limitation, transplantation of one or more follicles, including all or a fraction of an ovary, to a kidney capsule, to a subcutaneous site, to an ovarian site, e.g. where one ovary has been retained and one has been removed for ex vivo treatment, the one or more treated follicles may be transplanted to the site of the remaining ovary.

In some embodiments, in vitro treatment is followed by ovarian transplantation to activate primordial or primary follicles for the generation of preovulatory oocytes, which may be followed by in vitro or in vivo fertilization.

Individuals of interest include endangered species, economically important animals, women suffering from premature ovarian failure, follicles derived from human embryonic stem cells and primordial germ cells, and the like. In other embodiments, the exposure is performed in vivo, locally, e.g. by intra-ovarian injection, or systemically administered to an individual.

Following exposure to an R-spondin or CNP agonist, the individual may be treated with follicular stimulating hormone (FSH) or FSH analogs, including recombinant FSH, naturally occurring FSH in an in vivo host animal, FSH analogs, e.g. FSH-CTP, pegylated FSH, and the like, at a concentration that is effective to initiate follicular growth.

Where the follicles have been stimulated to the antral stage, either with CNP, FSH, or agonists thereof, the individual may be treated lutenizing hormone (LH) or an agonist thereof, which agonists specifically include chorionic gonadotropins, e.g. equine chorionic gonadotropin (eCG), human chorionic gonatotropin (HCG), etc., at an ovulatory dose. In addition, the follicles may be exposed in vivo or in vitro to one or more of c-kit ligand, neurotrophins, vascular endothelial growth factor (VEGF), bone morphogenetic protein (BMP)-4, BMP7, leukemia inhibitory factor, basic FGF, keratinocyte growth factor; and the like.

The term "R-spondin agonist" specifically includes R-spondin 1 protein and R-spondin 2 protein, e.g. the native human protein, or protein derived from a mammal of interest, fusion or chimeras of a native protein, e.g. fusion products with a portion of an immunoglobulin; pegylated version of the native protein, in addition to antibodies and other mimetics that provide for the biological activity of an R-spondin.

The term "CNP agonist" specifically includes CNP peptides, e.g. the native human polypeptide, or a counterpart derived from a mammal of interest, fusion or chimeras of a native polypeptide; stabilized versions of the native peptide, in addition to antibodies and other mimetics that provide for the biological activity of CNP.

The period of time effective for stimulation with an R-spondin or CNP agonist according to the methods of the invention is usually at least about one hour and not more than about 5 days, and may be at least about 12 hours and not more than about 4 days, e.g. 2, 3, 4 or 5 days.

FSH treatment has been used extensively for the stimulation of follicle development to generate mature oocytes for fertilization. Our findings demonstrated that CNP could also stimulate both preantral and antral follicles, thus providing future opportunities for treatment of infertile women using this peptide hormone.

BRIEF DESCRIPTION OF THE FIGURES

FIG. 1A-1D: Expression of R-spondin2 together with different Wnt ligands, and Frizzled receptors in different ovarian cell types. FIG. 1A) In situ hybridization analyses of R-spondin2 transcripts in ovaries of neonatal (day 3, a and b), juvenile (day 15, c and d), and prepubertal (day 23, e and f) mice were analyzed. Left panels: bright-field images; right panels: dark-field images. Scale bars=100 um. Arrowheads: oocytes. FIG. 1B) Real-time RT-PCR analyses of R-spondin2 transcripts in isolated oocytes and somatic cells of preantral follicles. Ovaries from immature mice at 10 days of age containing secondary and smaller follicles were dissociated to obtain oocytes and somatic cells. The purity of these cells was confirmed using specific markers (GDF9 for oocyte, FSH receptor for somatic cells). U.D.: undetectable. FIG. 1C). Real time RT-PCR analyses of different Wingless (Wnt) gene transcripts in oocytes and somatic cells. U.D.: undetectable. FIG. 1D) Real time RT-PCR analyses of different frizzled (FZD) gene transcripts in oocytes and somatic cells.

FIG. 2A) Synergistic stimulation of TCF-luciferase reporter activity by R-spondin2 and Wnt3A in cultured somatic cells obtained from ovaries of mice at 10 days of age. Cells were transfected with the TCF-luciferase reporter plasmid for 6 h before treatment with different reagents for 18 h. C: control; Rspo2: R-spondin2; DKK1: 300 ng/ml; Wnt3a: 30 ng/ml; FSH: 100 ng/ml. FIG. 2B) Stimulatory effects of R-sponind2 and Wnt3a on MTS (3-(4,5-dimethylthiazol-2-yl)-5-(3-carboxymethoxyphenyl)-2-(4-sulfophenyl)-2H-tetrazolium) activity of cultured somatic cells to reflect cell numbers.

Cells were treated with different reagents for 2 days before analyses of MTS activity. C; controls; *P<0.05 vs. controls.

Figure 3A:
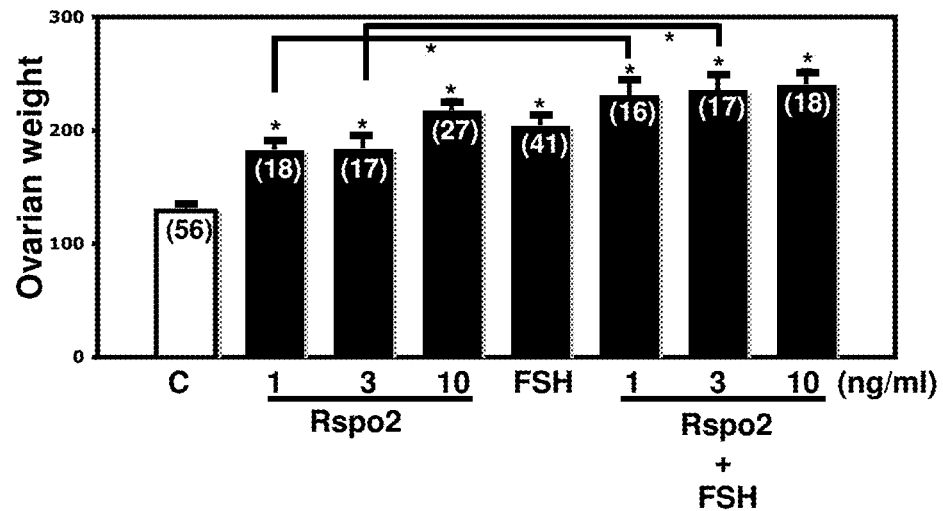
Figure 3B:
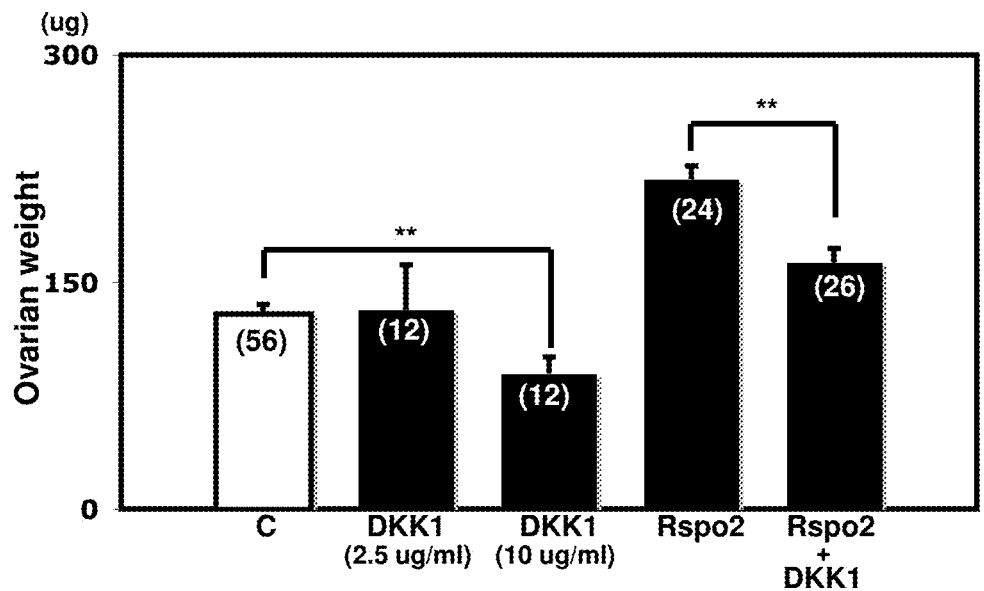
Figure 3C:
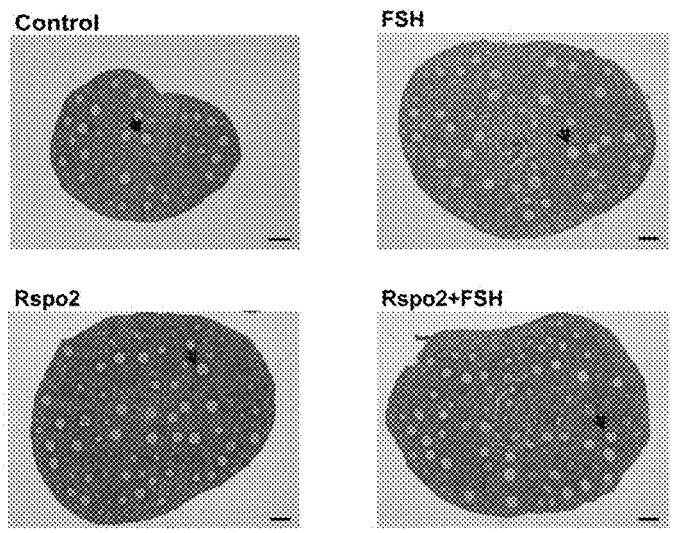
Figure 3D:
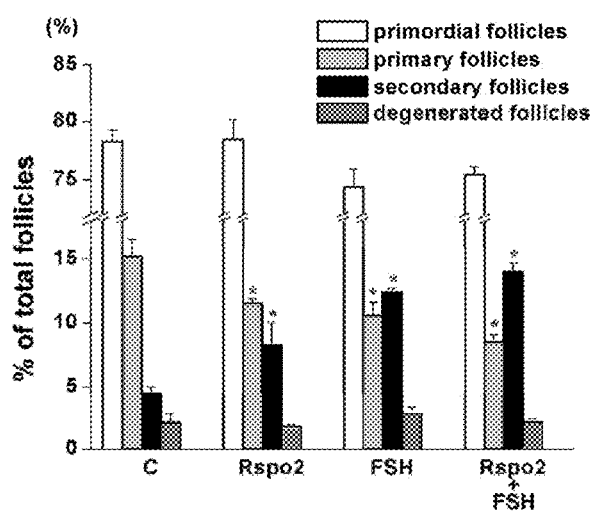
Figure 3E:
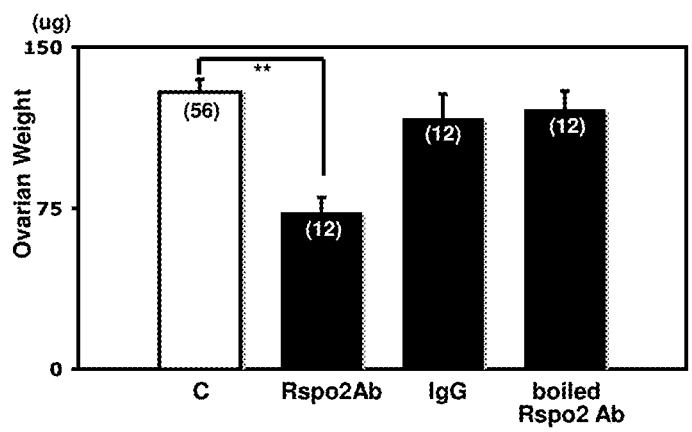

FIG. 3A-3E: Treatment with R-spondin2 and FSH stimulated early follicle growth in vitro and the role of endogenous R-spondin2. Explant cultures of individual ovaries from mice at day 10 of age were incubated with different reagents for 4 days with media changes at day 2 of culture. Some ovaries were treated with DKK1 (Dickkopf1, a Wnt signaling antagonist) to suppress the Wnt signaling pathway. FIG. 3A) Ovarian weight changes after treatment with R-spondin2 and FSH. FIG. 3B) Antagonistic effects of DKK1 on basal and R-spondin2-stimulated ovarian weight. FIG. 3C) Histology of ovaries treated with R-spondin2 and/or FSH. Arrowheads: secondary follicles. FIG. 3D) Follicle dynamics following treatment with R-spondin2 and FSH. FIG. 3E) Treatment with R-spondin2 antibodies decreased ovarian weight by blocking the actions of endogenous R-spondin2 in ovarian explants. Co-incubation with non-immune IgG and boiled R-spondin2 antibodies (Ab) served as controls. R-spo2: R-spondin2.

Figure 4A:
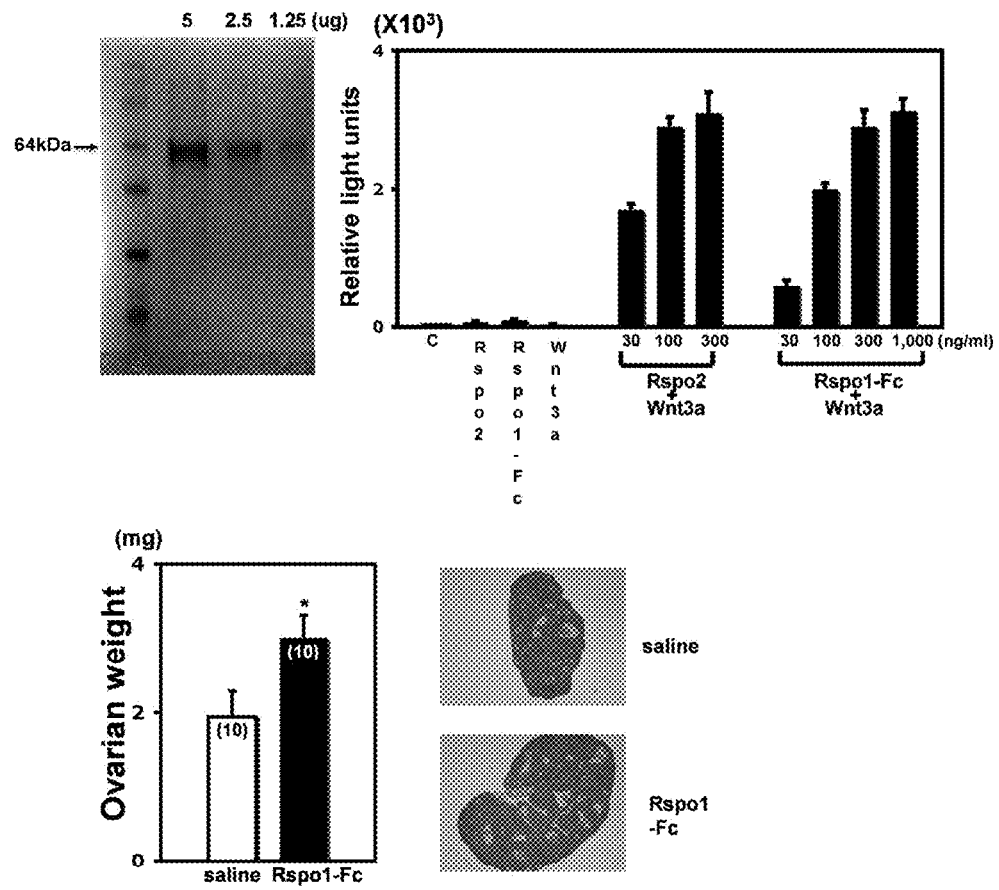
Figure 4B:
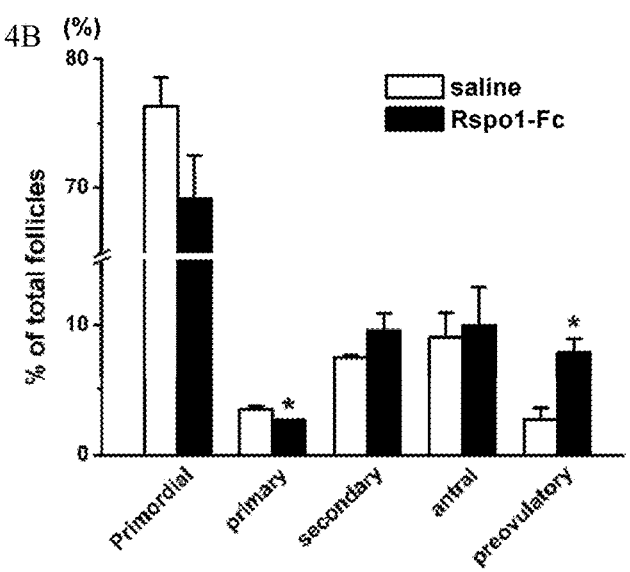
Figure 4C:
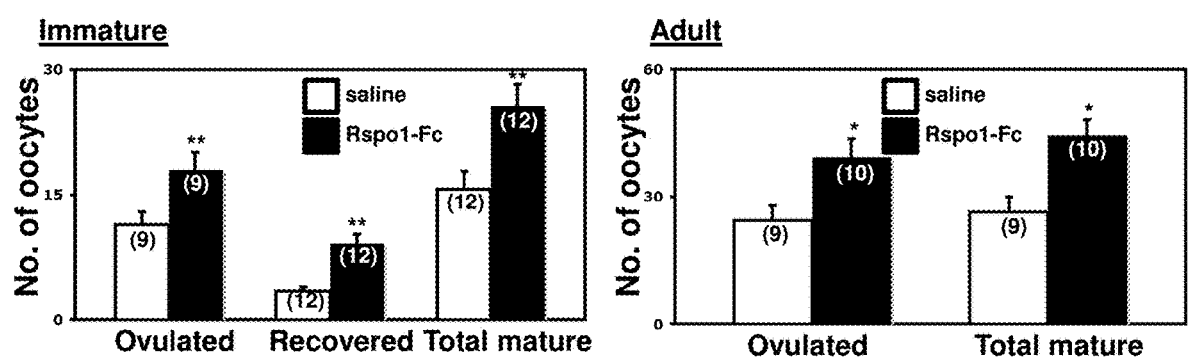
Figure 4D:
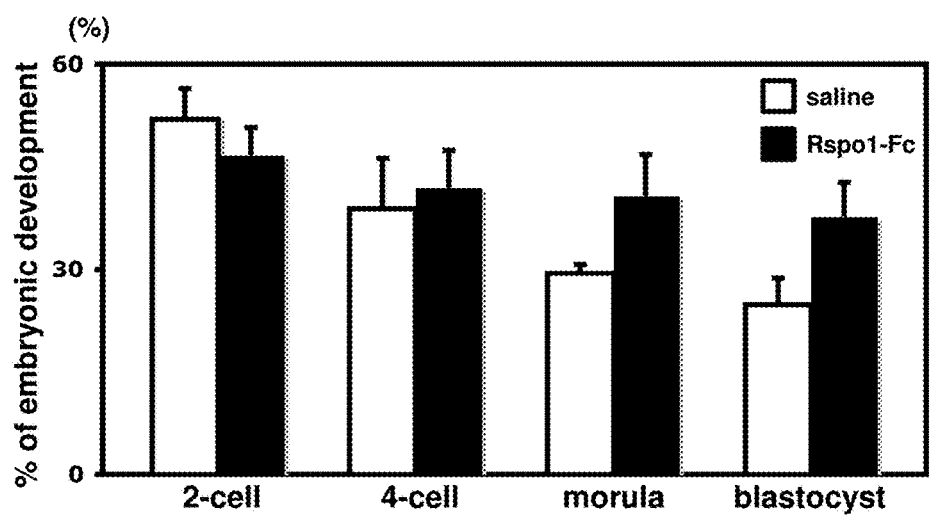

FIG. 4A-4D: Treatment with R-Spondin1-Fc stimulated the development of early ovarian follicles to allow the generation of mature oocytes for fertilization and early embryonic development. FIG. 4A) Purification of recombinant R-spondin1-Fc and its stimulation of the canonical Wnt signaling pathway. Left panel: immunostaining and Coomassie Blue staining of R-spondin1-Fc. Right panel: TCF-luciferase assay. 293T cells were transfected with TCF-luciferase reporter plasmids before treatment with different doses of R-spondin2 or R-spondin1-Fc. FIG. 4B) Increases in ovarian weight and follicle development after treatment with R-spondin1-Fc in mice. Prepubertal mice at day 10 of age were injected ip with R-spondin1-Fc (10 µg/day) or saline daily for 5 days followed by eCG treatment for 2 days for ovarian weight determination. Left panel: ovarian weight; Middle panel: histology; right panel: follicle dynamics. FIG. 4C) Treatment with R-spondin1-Fc increased ovulation efficiency. Immature mice pretreated with R-spondin1-Fc followed by eCG were injected with a single dose (7 IU) of hCG to induce ovulation. Some adult mice were pretreated with a GnRH antagonist (1 µg/g body weight) for 4 days before i.p. treatment with R-spondin1-Fc or saline daily for 4 more days. Animals were then treated with eCG for 48 h followed by hCG to induce ovulation and oocyte maturation. At 16 h after hCG injection, numbers of ovulated mature eggs in oviducts were determined. Mature oocytes were also punctured from ovaries to allow the determination of total mature oocytes for each group. Numbers above the bars indicate the number of animals used. FIG. 4D) Development of early embryos after in vitro fertilization of mature oocytes obtained from adult mice treated with R-spondin1-Fc. Ovulated oocytes obtained from the oviducts were inseminated with sperm in vitro and early embryonic development monitored daily for 4 days. Percentages of mature oocytes developed into different stages of early embryos were determined.

Figure 5A:
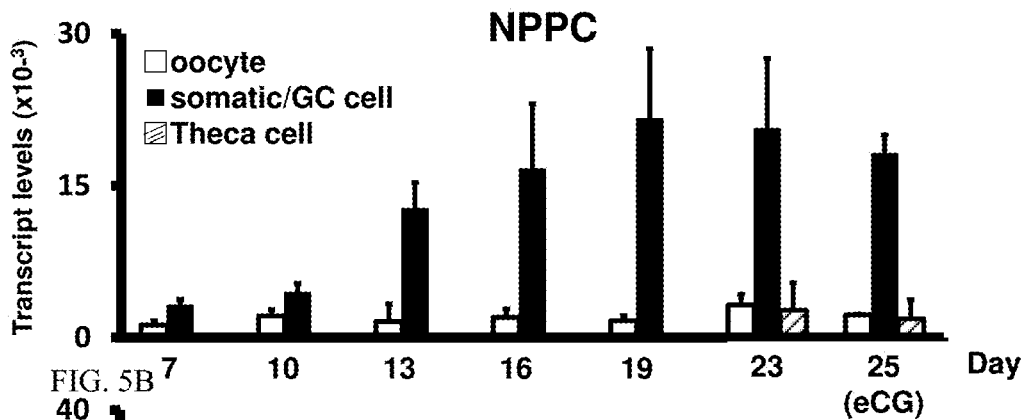
Figure 5B:
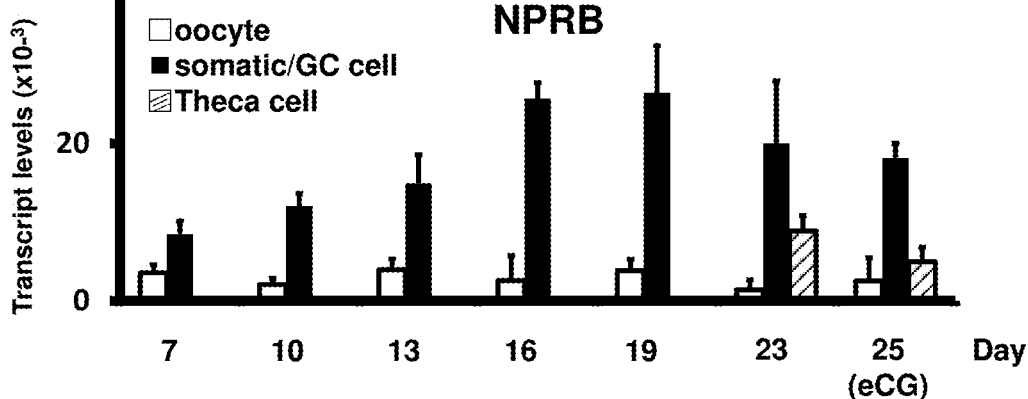
Figure 5C:
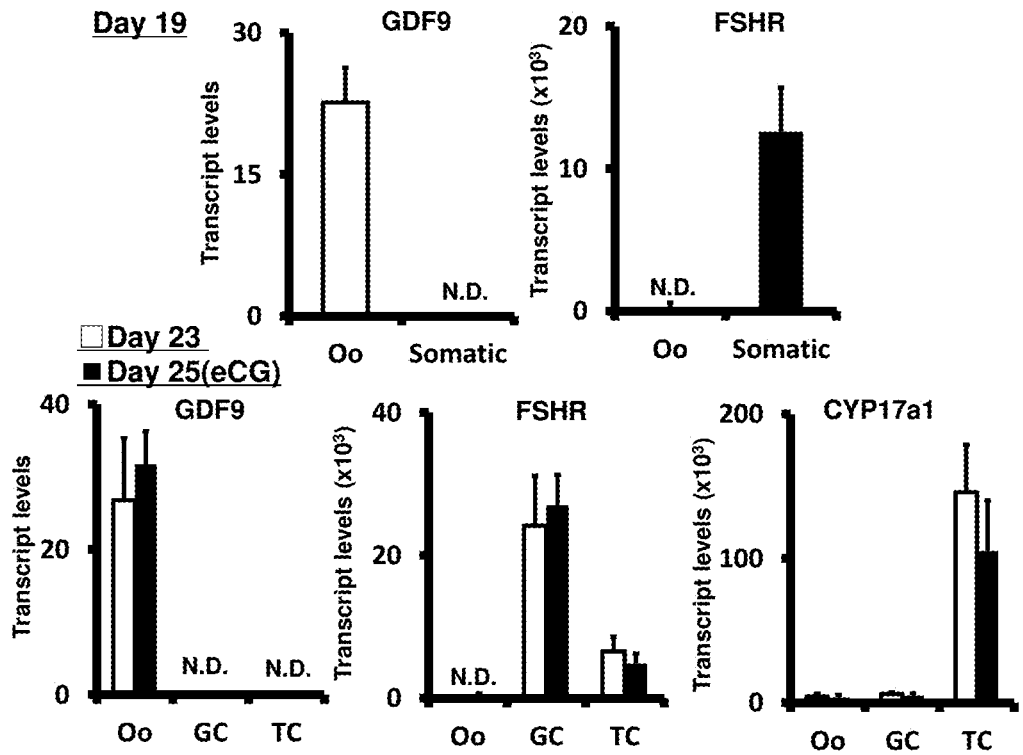
Figure 5D:
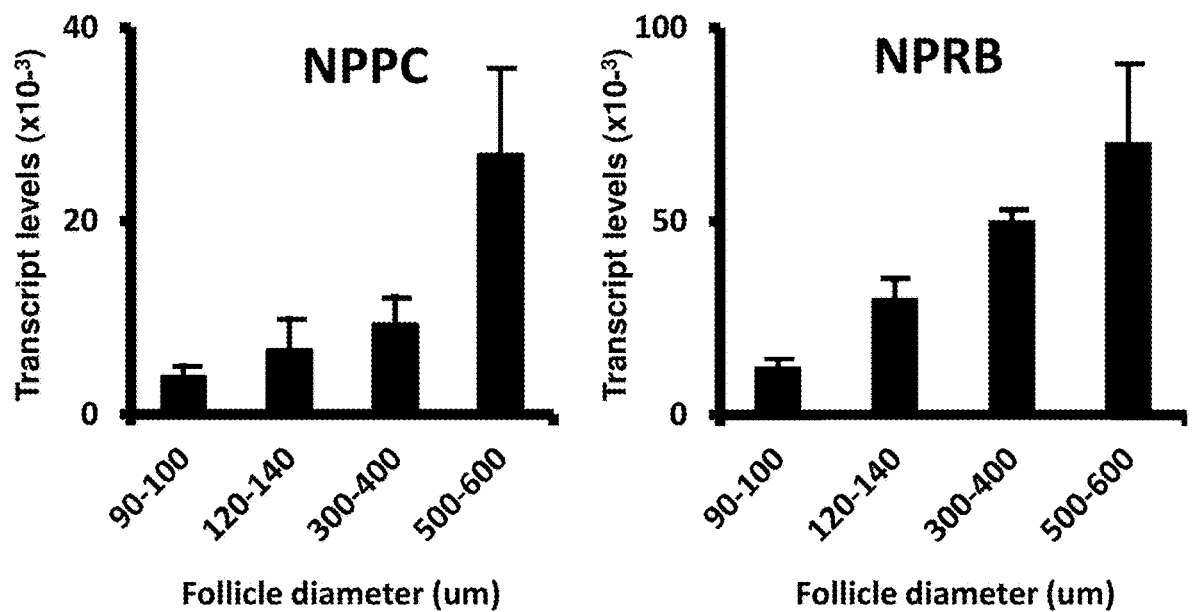
Figure 5E:
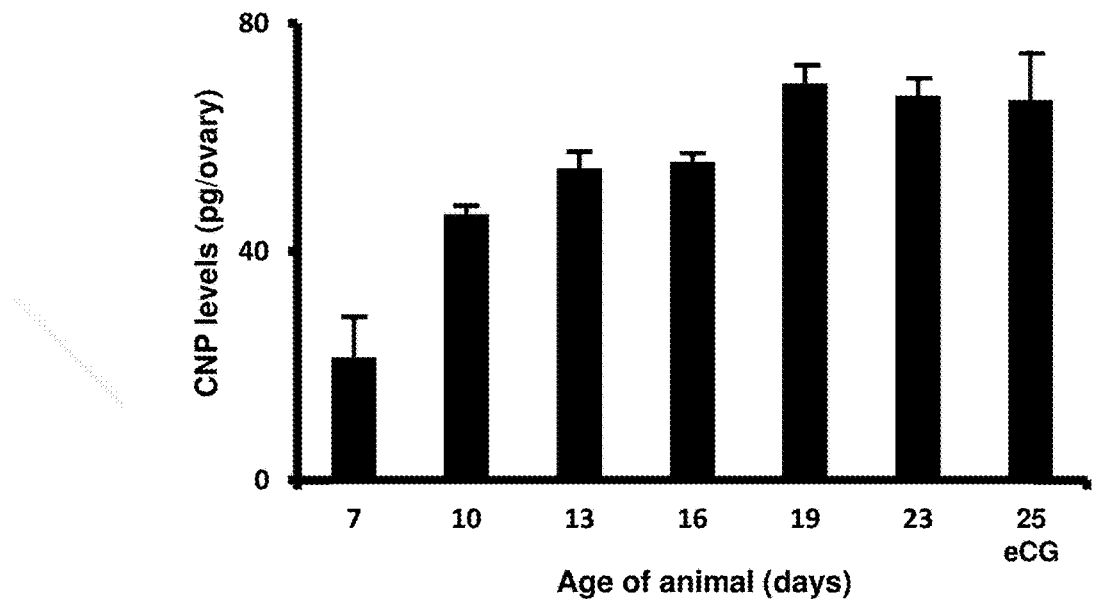

FIG. 5A-5E: Ovarian expression of NPPC and NPRB as well as ovarian CNP peptide content during development. Ovaries from immature mice at different ages were dissociated to obtain oocytes and somatic cells. In addition, granulosa cells, theca shell, and oocytes from immature mice at day 23 of age before and after eCG treatment for 2 days were isolated. Real-time RT-PCR was performed using specific primers. The purity of different cell types was confirmed using specific markers (GDF9 for oocyte, FSH receptor for granulosa cells, and CYP17a1 for theca cells). FIG. 5A) Expression of NPPC, FIG. 5B) Expression of NPRB, FIG. 5C) Expression of cell markers, N. D.: not detectable, OC: oocyte. FIG. 5D) RT-PCR of NPPC and NPRB transcripts in isolated follicles of different sizes. Follicles (1-5 follicles/sample) of different diameters were isolated from juvenile (90-140 nm in diameter) and eCG-treated immature mice (300-600 um in diameter) for analyses. FIG. 5E) Measurement of ovarian CNP content from pubertal mice at different ages. Mean+/−SE of 6-8 samples.

Figure 6A:
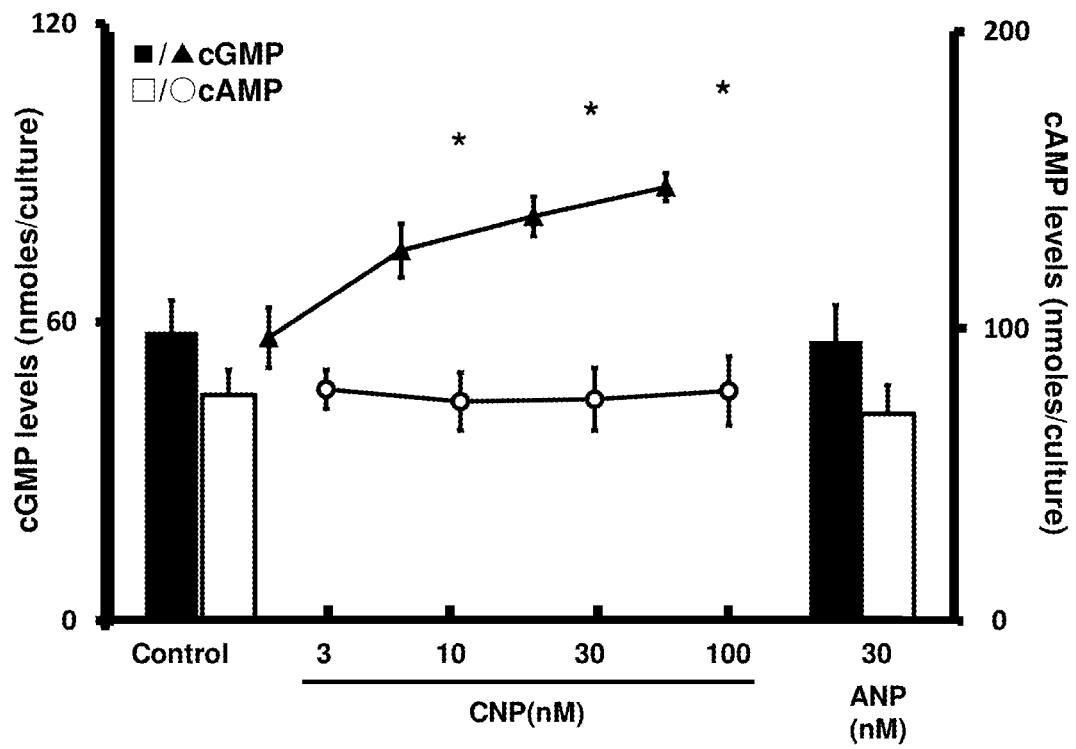
Figure 6B:
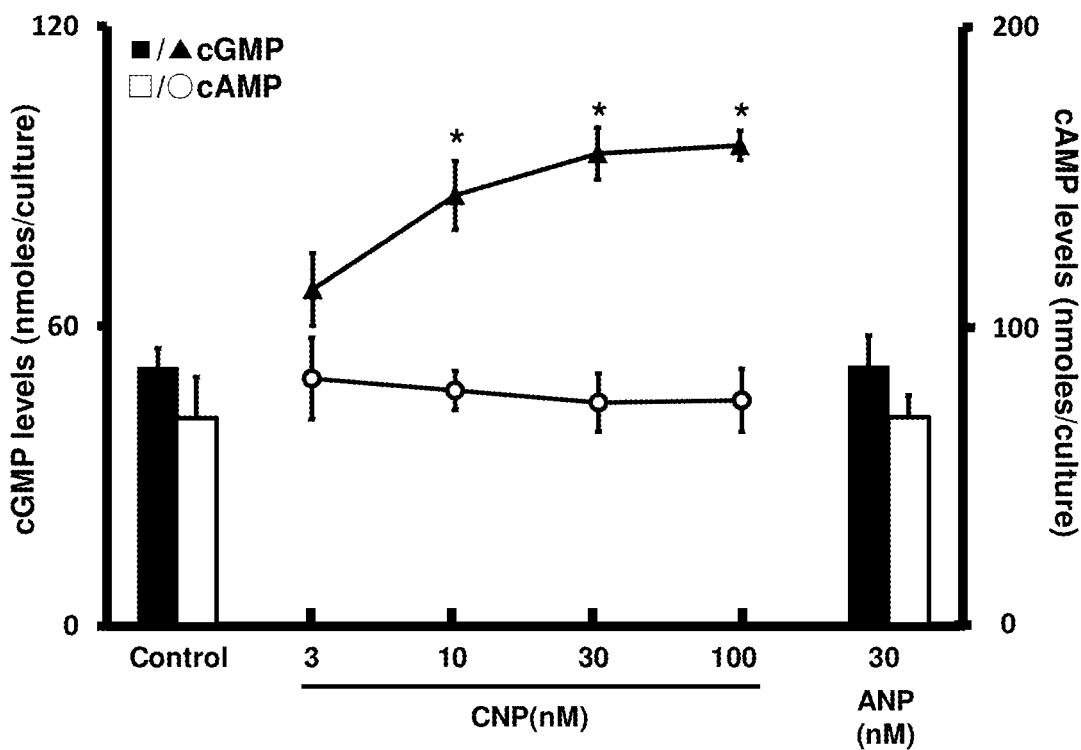

FIG. 6A-6B: CNP stimulation of cGMP, but not cAMP, production by cultured somatic and granulosa cells. FIG. 6A) CNP stimulation of cGMP production by cultured somatic cells. Somatic cells isolated from mice at day 13 of age were treated with CNP and ANP in media containing IBMX. At 2 h after incubation, media content of cGMP and cAMP was measured. FIG. 6B) CNP stimulation of cGMP production by cultured granulosa cells from prepubertal mice at 21 days of age. Granulosa cells were punctured from ovaries of prepubertal mice and treated with different reagents for 2 h before measurement of media content of cGMP and cAMP. Mean+/−SE of 8 samples. *, P<0.05, significantly different from the control group.

Figure 7A:
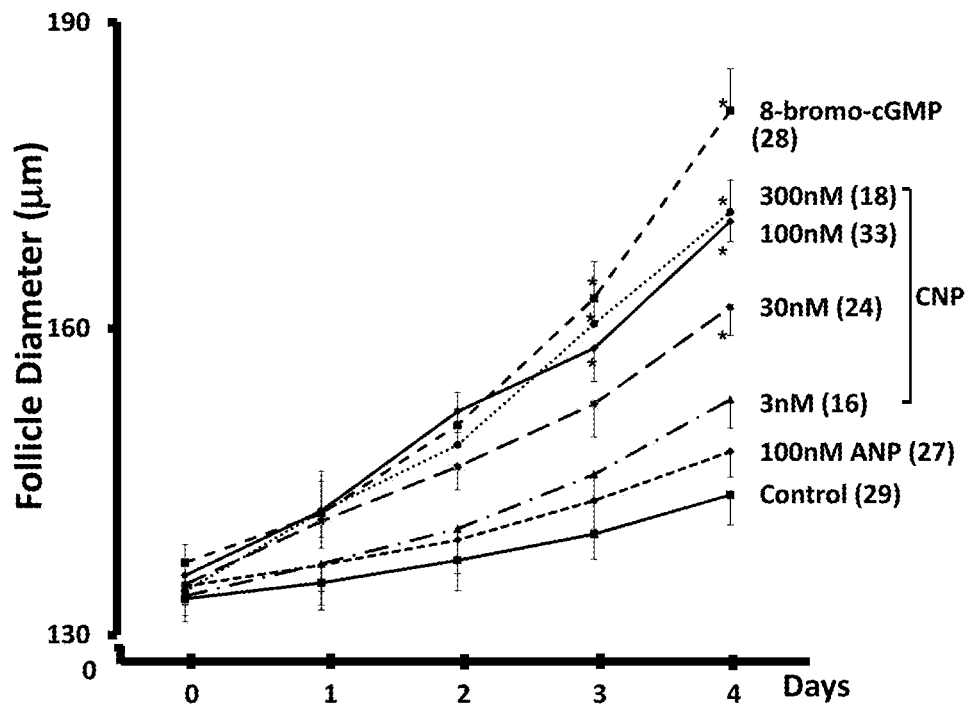
Figure 7B:
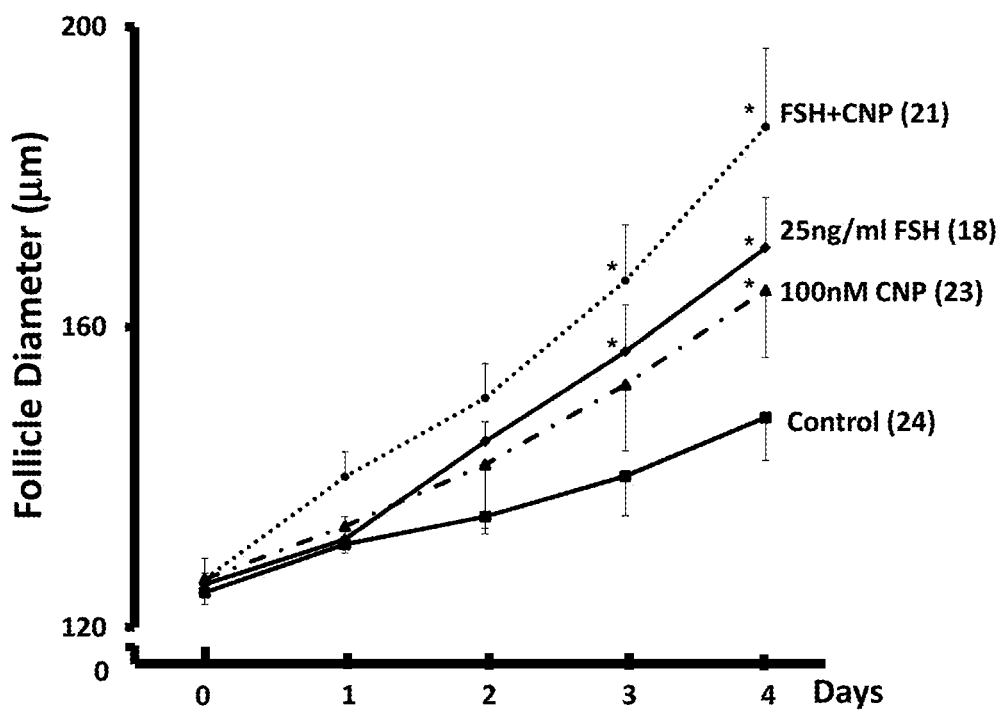

FIG. 7A-7B: CNP promotion of preantral follicle growth in culture. Preantral follicles (125-145 um) were isolated from mice at day 13 of age and cultured for 4 days with media changes every two days. FIG. 7A) Follicles were treated with increasing doses of CNP (3-300 nM), 100 nM ANP, or 8-bromo-cGMP (5 mM), and follicle diameters monitored daily. FIG. 7B) Additive effects of CNP and FSH. Preantral follicles were treated with FSH (25 ng/ml) and/or CNP (100 nM). Numbers of follicles used are shown in parenthesis. Mean+/−SE. *, P<0.05, significantly different from the control group.

Figure 8A:
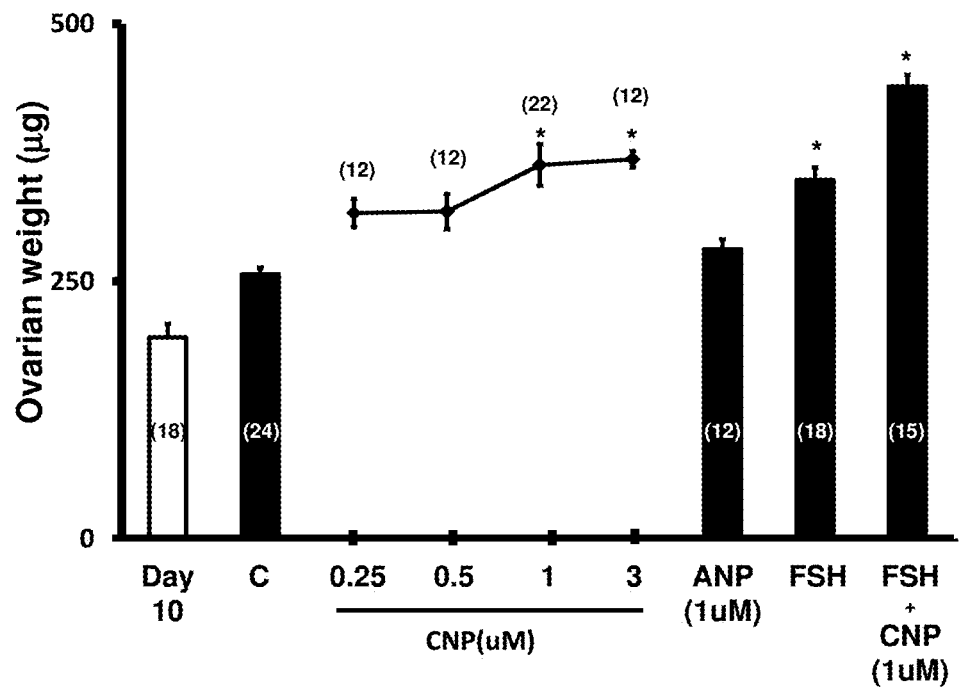
Figure 8B:
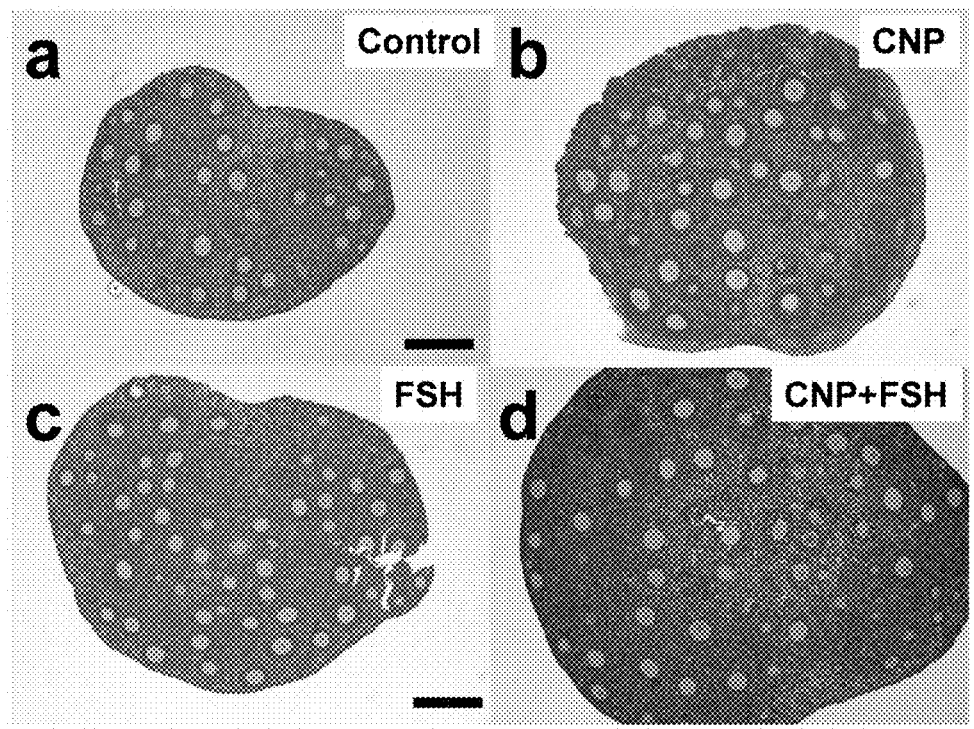
Figure 8C:
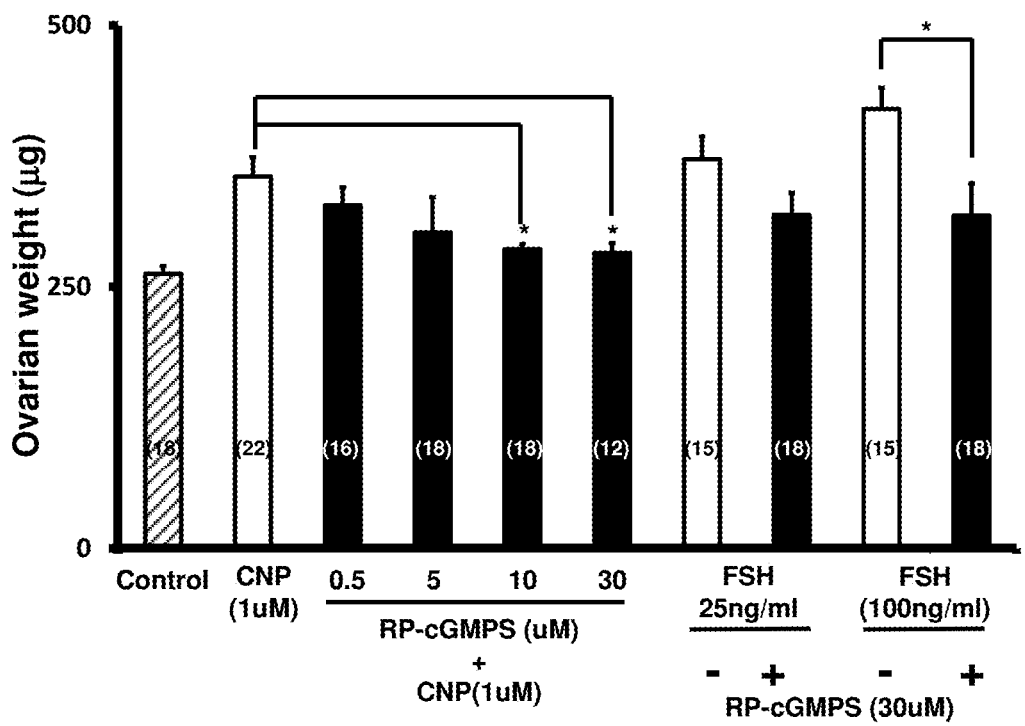
Figure 8D:
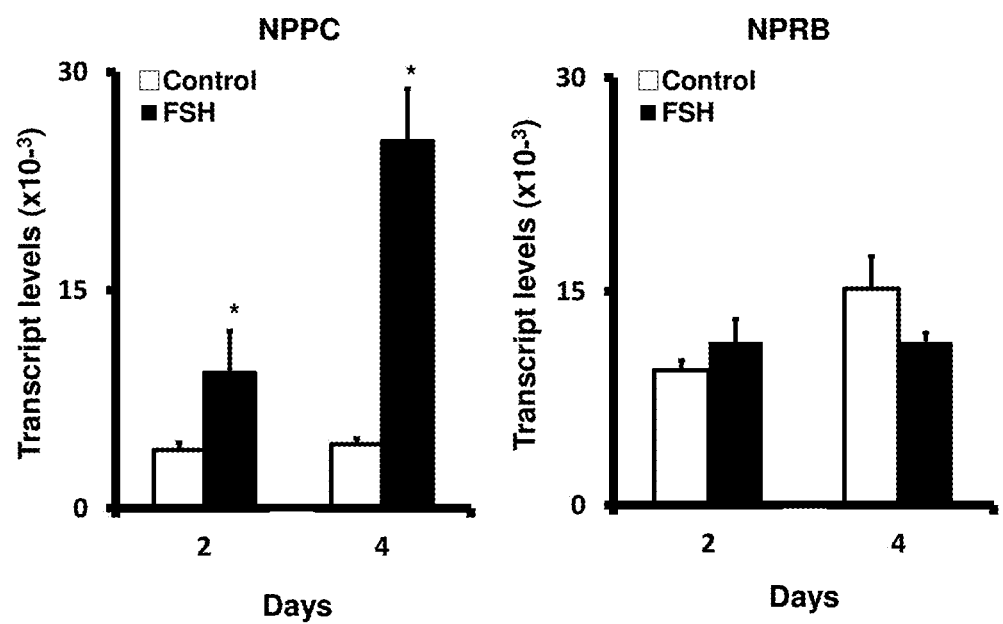

FIG. 8A-8D: CNP stimulation of the growth of ovarian explants and FSH stimulation of NPPC expression. FIG. 8A) Individual ovaries from mice at day 10 of age were cultured with increasing doses (0.25-3 uM) of CNP, ANP (1 uM) or FSH (25 ng/ml) with or without CNP for 4 days with media changes every 2 days. Ovarian weights were determined at the end of culture. FIG. 8B) Histological analyses of ovarian explants. Ovarian explants at 4 days after treatment with CNP and/or FSH were fixed for histological analyses. Bars: 400 um. FIG. 8C) Treatment with a pan-specific protein kinase G inhibitor, Rp-8-Br-PET-cGMPS (Rp-cGMPS) blocked the CNP stimulation of ovarian weight gain. Treatment with Rp-cGMPS also partially blocked the stimulatory effects of a high dose (100 ng/ml) of FSH. FIG. 8D) FSH stimulation of NPPC but not NPRB transcript levels in cultured ovarian explants. Ovarian explants from mice at day 10 of age were cultured for 2 and 4 days before measurement of NPPC and NPRB transcript levels. Numbers of ovaries used are shown in parenthesis. Mean+/−SE *, P<0.05, significantly different from the control group.

Figure 9A:
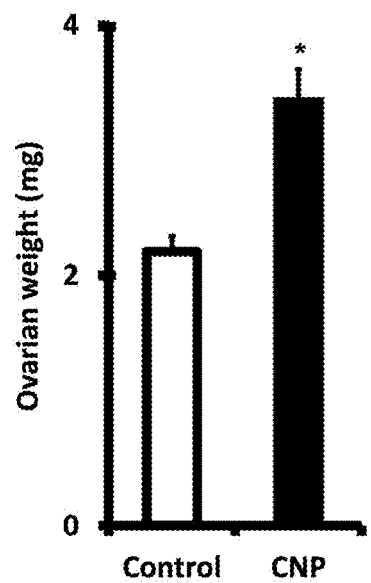
Figure 9B:
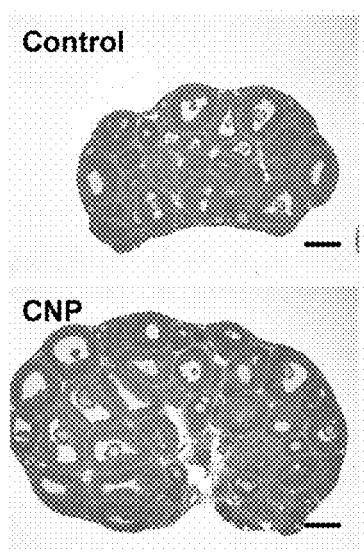
Figure 9C:
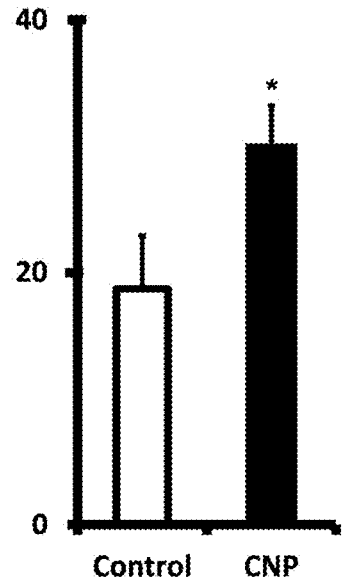

FIG. 9A-9C: In vivo treatment of juvenile mice with CNP promoted the development of preantral follicles. Mice at day 13 of age were treated i.p. with CNP (20 µg/kg body weight) daily for 4 days to stimulate the development of preantral follicles. Some animals pretreated with CNP were further treated i.p. with eCG (5 IU) for 48 h, followed by an ovulatory dose of hCG (5 IU). Numbers of ovulated oocytes in oviducts were determined. FIG. 9A) ovarian weights; FIG. 9B) ovarian histology; FIG. 9C) ovulation efficiency. N=20 animals. Mean+/−SE *, P<0.05, significantly different from the control group.

Figure 10A:
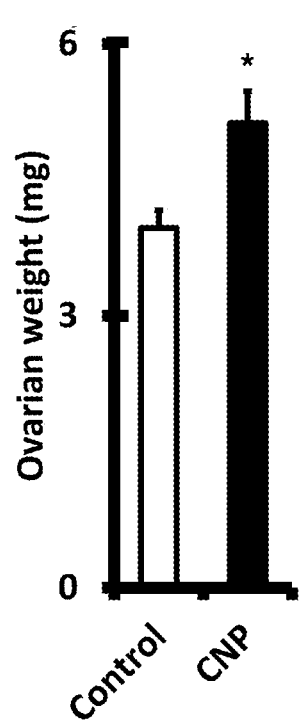
Figure 10B:
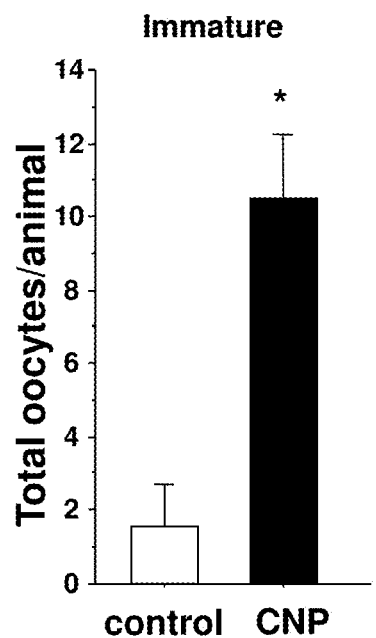

FIG. 10A-10B: In vivo treatment with CNP promoted the growth of early antral follicles into the preovulatory stage for ovulation in immature mice. FIG. 10A and FIG. 10B) Prepubertal mice at day 21 of age were treated with CNP (50 ug/kg body weight) or saline daily for 4 days before ovulation induction with hCG (2.5 IU). At 18 h after hCG treatment, ovarian weights were determined and mature oocytes in oviducts were counted. Human follicles Mean+/−SE *, P<0.05, significantly different from the control group.

Figure 11:
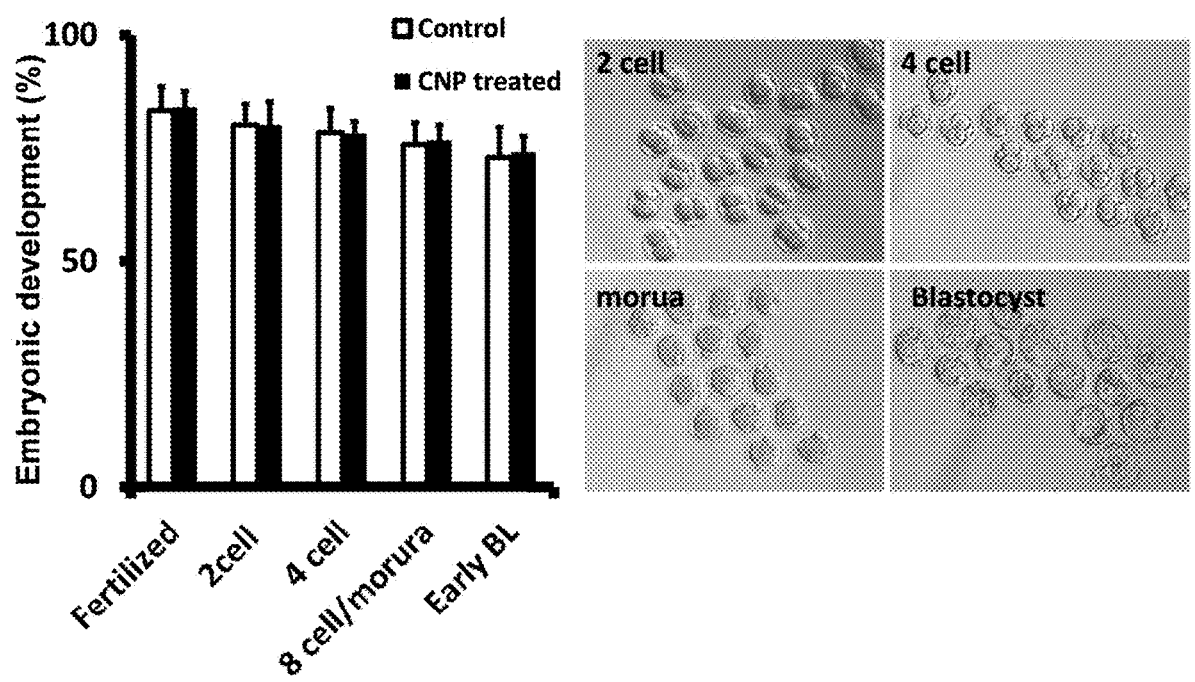

FIG. 11: Early embryonic development of oocytes derived from immature mice pretreated with CNP to stimulate the preovulatory follicle development. Mature oocytes were obtained from immature mice (21 days of age) pretreated with CNP for four days, followed by an ovulatory dose of hCG. Oocytes were fertilized with viable sperm in vitro and cultured for different periods. Oocytes from the control group were derived from immature mice treated with 5 IU eCG for 2 days followed by an ovulatory dose of hCG for 18 h. Development of early embryos was determined based on morphology. Left panel: ratios of embryos reaching different developmental stages. BL: blastocyst. Right panel: embryo morphology of CNP-pretreated oocytes.

DESCRIPTION OF THE SPECIFIC EMBODIMENTS

Compositions and methods are provided for modulating the survival and maturation of mammalian ovarian follicles. By selectively exposing follicles to an effective dose of at least one of an R-spondin agonist or a CNP agonist, follicle growth and consequent oocyte maturation can be manipulated.

The methods of the invention find use in a wide variety of animal species, particularly including mammalian species. Animal models, particularly small mammals, e.g. murine, lagomorpha, etc. are of interest for experimental investigations. Other animal species may benefit from improvements in in vitro fertilization, e.g. horses, cattle, rare zoo animals such as panda bears, large cats, etc. Humans are of particular interest for enhancing oocyte maturation, including methods of in vitro fertilization. Individuals of interest for treatment with the methods of the invention include, without limitation, those suffering from premature ovarian failue, perimenopause, FSH low responsiveness, etc.

Embodiments of the invention can include ovarian follicles of numerous species of mammals. The invention should be understood not to be limited to the species of mammals cited by the specific examples within this patent application. Embodiments of the invention, for example, may include fresh or frozen-thawed follicles of animals having commercial value for meat or dairy production such as swine, bovids, ovids, equids, buffalo, or the like (naturally the mammals used for meat or dairy production may vary from culture to culture). It may also include ovarian follicles from individuals having rare or uncommon attribute(s), such as morphological characteristics including weight, size, or conformation, or other desired characteristics such as speed, agility, intellect, or the like. It may include ovarian follicles from deceased donors, or from rare or exotic mammals, such as zoological specimens or endangered species. Embodiments of the invention may also include fresh or frozen-thawed ovarian follicles collected from primates, including but not limited to, chimpanzees, gorillas, or the like, and may also ovarian follicles from marine mammals, such as whales or porpoises.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Ovarian follicle. An ovarian follicle is the basic unit of female reproductive biology and is composed of roughly spherical aggregations of cells found in the ovary. A follicle contains a single oocyte. Follicles are periodically initiated to grow and develop, culminating in ovulation of usually a single competent oocyte. The cells of the ovarian follicle are the oocyte, granulosa cells and the cells of the internal and external theca layers. The oocyte in a follicle is in the stage of a primary oocyte. The nucleus of such an oocyte is called a germinal vesicle. Granulosa cells within the follicle surround the oocyte; their numbers increase in response to gonadotropins. They also produce peptides involved in ovarian hormone synthesis regulation. Follicle-stimulating hormone (FSH) acts on granulosa cells to express luteinizing hormone (LH) receptors on the cell surface. The granulosa cells, in turn, are enclosed in a thin layer of extracellular matrix—the follicular basement membrane or basal lamina (fibro-vascular coat in picture). Outside the basal lamina, the layers theca interna and theca externa are found.

Ovarian in vitro culture. Methods are known in the art for culturing mammalian ovaries or fragments thereof, which fragments for the purposes of the present invention will include at least one follicle. Typically all or a portion of an ovary is placed in tissue culture medium, which medium may include factors useful in the growth or maintenance of the follicle cells, and may, as described herein, further comprise an effective dose of a PTEN inhibitor. See the Examples provided herein. Additional description may be found, inter alia, (each of which reference is herein specifically incorporated by reference) at Hoyer et al. (2007) Birth Defects Res B Dev Reprod Toxicol. 80 (2):113-25. In vitro culture of canine ovaries is described by Luvoni et al. (2005) Theriogenology; 63 (1):41-59. Culture of bovine follicles is described by Hansel (2003) Anim Reprod Sci.; 79 (3-4): 191-201. Fortune (2002) Ernst Schering Res Found Workshop. (41):11-21 describes organ cultures using small pieces of ovarian cortex, or grafts of ovarian cortical pieces beneath the CAM of chick embryos.

A review of in vitro ovarian tissue and organ culture may be found in Devine et al. (2002) Front Biosci. 7:d1979-89; and in Smitz et al. (2002) Reproduction. 123 (2):185-202. Whole ovaries from fetal or neonatal rodents have been incubated in organ culture systems. This has been utilized to understand the sequence of follicle formation and its hormonal requirements, activation of quiescent follicles, follicular growth and development, and acquisition of steroidogenic capabilities. Adaptations of this technique include incubation of ovaries in a chamber continuously perfused with medium or perfusion of medium through the intact vasculature. Late follicular development, ovulation, and steroidogenesis can also be examined in these systems. Another approach has been to culture individual follicles isolated by enzymatic or mechanical dissociation. Cryopreservation of human primordial and primary ovarian follicles is described by Hovatta (2000) Mol Cell Endocrinol. 169 (1-2):95-7.

Ovarian transplantation. Starting in 1950s, ovarian transplantation to the kidney is a well-established procedure in animal studies. Later on, primordial follicles isolated from infant mouse ovaries by enzymatic digestion were transplanted into ovarian bursa of adult hosts sterilized by X-irradiation or ovariectomy. Ovaries forming from grafts were capable of spontaneous ovulation and the majority of animals carrying them were receptive to males. Mating often resulted in pregnancies and delivery of normal offspring. Furthermore, primordial follicles can be cryopreserved before transplantation. In women, successful ovarian transplantation between monozygotic twins discordant for premature ovarian failure has been reported. After unsuccessful egg-donation therapy, the sterile twin received a transplant of ovarian cortical tissue from her sister. After transplantation, the patient became pregnant and delivered a healthy baby. In addition to this case of ovarian transplantation, autologous transplantation of ovarian cortical strips to the forearm has been successfully performed in women undergoing sterilizing cancer therapy or surgery as demonstrated by the preservation of endocrine functions. Here, the ovarian transplantation approach may be used to activate dormant primordial follicles.

R-spondin 2 (RSPO2). R-spondins (RSPOs), such as RSPO2, are secreted proteins that regulate beta-catenin through binding to Frizzled 8 and LRP6 receptors. Like other members of the RSPO family, the 243-amino acid human RSPO2 protein contain an N-terminal signal peptide, 2 furin-like domains, a thrombospondin type-1 domain, and a C-terminal low-complexity region enriched with positively charged amino acids. RSPO2 expression has been detected in organs of endodermal origin, including colon, rectum, small intestine, and lung, with decreased expression in corresponding tumors. RSPO2 functions in a positive feedback loop to stimulate the WNT/beta-catenin cascade. The human RSPO2 gene contains 6 coding exons, and maps to chromosome 8q23.1.

The genetic reference sequence for R-spondin 2 may be accessed at Genbank, locus NM_178565, and as described by Clark et al. (2003) Genome Res. 13 (10), 2265-2270, herein specifically incorporated by reference.

"R-spondin1" protein is described in Genbank Accession NP_001033722. R-spondin1 (R-spo1) is one of the four proteins in the R-spondin protein family (Four human paralogs of R-spondin include R-spondin1-4). R-spo1 is a secreted glycoprotein containing a leading signal peptide, two cysteine-rich, furin-like domains, and one thrombospondin type 1 domain. R-Spo1 has no homology with Wnts, but synergizes with Wnts to activate β-catenin-dependent signaling.

Included in the R-spondin molecules of interest, e.g. R-spondin 1 and R-spondin 2 are "chimeric" polypeptides comprising a R-spondin polypeptide or portion (e.g., one or more domains) thereof fused or bonded to heterologous polypeptide. The chimeric polypeptide will generally share at least one biological property in common with a native R-spondin polypeptide. Examples of chimeric polypeptides include immunoadhesins, which combine a portion of the native polypeptide with an immunoglobulin sequence, particularly an Fc region of an immunoglobulin, which molecules are known in the art to provide for improved pharmacokinetic properties. For example, a commercially available product is the full-length human R-Spondin-1 fused at its C-terminus to the Fc domain of human IgG1. This fusion increases the stability of the protein in vitro and in vivo without compromising its biological activity. See de Lau, et al (2011) Nature 476: 293; Carmon et al. (2011) PNAS 108: 11452, each herein specifically incorporated by reference.

Where the activating agent is an R-spondin protein or fusion thereof, e.g. R-spondin 1-Fc, for in vivo use the effective dose may be at least about 0.1 µg/kg body weight/day, at least about 0.5 µg/kg body weight/day, at least about 1 µg/kg body weight/day, at least about 2.5 µg/kg body weight/day, at least about 5 µg/kg body weight/day, at least about 10 µg/kg body weight/day, at least about 20 µg/kg body weight/day, at least about 25 µg/kg body weight/day, at least about 50 µg/kg body weight/day, at least about 85 µg/kg body weight/day, at least about 100 µg/kg body weight/day, at least about 250 µg/kg body weight/day, at least about 500 µg/kg body weight/day. For in vitro use the concentration of an R-spondin may be at least about 0.5 ng/ml, at least about 1 ng/ml, at least about 2.5 ng/ml, at least about 5 ng/ml, at least about 7.5 ng/ml, at least about 10 ng/ml or more.

CNP. Natriuretic peptides comprise a family of three structurally related molecules: atrial natriuretic peptide (ANP), brain natriuretic peptide (BNP), and C-type natriuretic peptide (CNP). CNP is encoded by the NPPC (Natriuretic peptide precursor C) gene which is expressed in diverse cell types in which the precursor NPPC protein is cleaved into the 22 amino acid peptide CNP. CNP activates its cognate receptor guanylyl cyclase B (GC-B), also known as natriuretic peptide receptor-B (NPRB), whereas ANP and BNP stimulate guanylyl cyclase (GC)-A, also known as natriuretic peptide receptor-A (NPRA). GC-A and GC-B are membrane-anchored guanylyl cyclase enzymes that signal via the production of the second messenger cGMP and undergo both homologous and heterologous desensitization, reflected by dephosphorylation of specific sites in the kinase-homology domain. ANP and BNP act as endocrine hormones to regulate blood pressure and volume, and inhibit cardiac hypertrophy. In contrast, CNP acts in an autocrine/paracrine fashion to induce vaso-relaxation and vascular remodeling, and to regulate bone growth.

Earlier studies have reported ovarian expression of NPPC and NPRB and their regulation by gonadotropins. A recent study demonstrated the expression of NPPC messenger RNA in granulosa cells and the ability of CNP to stimulate cGMP production in cumulus cells to inhibit meiotic resumption of oocytes, consistent with earlier identification of a small molecular weight oocyte maturation inhibitor (OMI) in follicular fluid and granulosa cell extracts. Subsequent studies indicated that the ovulatory LH surge decreased CNP levels in murine ovaries and human follicular fluid.

CNP is 22 amino acid residues in length, and an N-terminally elongated form with 53 amino acid residues has also been described. ANP, BNP, and CNP are highly homologous within the 17-residue ring structure formed by an intramolecular disulfide linkage. The genetic sequence for CNP may be accessed at Genbank, locus NM_024409. ANP and BNP act mainly as cardiac hormones, produced primarily by the atrium and ventricle, respectively. CNP was thought to be expressed mainly in the brain; however, other studies demonstrated production of CNP by cultured endothelial cells and by blood vessels in vivo with augmentation of production of CNP by various cytokines and growth factors showed that mural granulosa cells, which line the follicle wall, express Nppc mRNA, whereas cumulus cells surrounding oocytes express mRNA of the Nppc receptor Npr2, a guanylyl cyclase. Nppc increased cGMP levels in cumulus cells and oocytes and inhibited meiotic resumption in vitro. Meiotic arrest was not sustained in most Graafian follicles of Nppc or Npr2 mutant mice, and meiosis resumed precociously. Oocyte-derived paracrine factors promoted cumulus cell expression of Npr2 mRNA.

Where the activating agent is CNP, for in vivo use the effective dose at least about 0.1 μg/kg body weight/day, at least about 0.5 μg/kg body weight/day, at least about 1 μg/kg body weight/day, at least about 2.5 μg/kg body weight/day, at least about 5 μg/kg body weight/day, at least about 10 μg/kg body weight/day, at least about 20 μg/kg body weight/day, at least about 25 μg/kg body weight/day, at least about 50 μg/kg body weight/day, at least about 85 μg/kg body weight/day, at least about 100 μg/kg body weight/day, at least about 250 μg/kg body weight/day, at least about 500 μg/kg body weight/day. For in vitro use the concentration of CNP may be at least about 0.5 ng/ml, at least about 1 ng/ml, at least about 2.5 ng/ml, at least about 5 ng/ml, at least about 7.5 ng/ml, at least about 10 ng/ml or more.

Antibodies specific for R-spondin or CNP or epitopic fragments thereof, particularly agonistic antibodies, may be used in the methods of the invention. As used herein, the term "antibodies" includes antibodies of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a green fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

"Antibody specificity", in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens. Methods of determining specific antibody binding are well known to those skilled in the art, and can be used to determine the specificity of antibodies of the invention for a polypeptide.

Antibodies are prepared in accordance with conventional ways, where the expressed polypeptide or protein is used as an immunogen, by itself or conjugated to known immunogenic carriers, e.g. KLH, pre S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in E. coli, and the heavy and light chains mixed to further enhance the affinity of the antibody. Alternatives to in vivo immunization as a method of raising antibodies include binding to phage display libraries, usually in conjunction with in vitro affinity maturation.

FSH. Follicle-stimulating hormone (FSH) is a hormone synthesized and secreted by gonadotropes in the anterior pituitary gland. FSH regulates the development, growth, pubertal maturation, and reproductive processes of the human body. FSH and Luteinizing hormone (LH) act synergistically in reproduction. In females, in the ovary FSH stimulates the growth of immature Graafian follicles to maturation. Graafian follicles are the mature preovulatory follicle. Primary follicles mature to Graafian follicles. As the follicle grows, it releases inhibin, which shuts off the FSH production.

FSH is a dimeric glycoprotein. The alpha subunits of LH, FSH, TSH, and hCG are identical, and contain 92 amino acids. FSH has a beta subunit of 118 amino acids (FSHB), which confers its specific biologic action and is responsible for interaction with the FSH-receptor. The half-life of native FSH is 3-4 hours. Its molecular wt is 30000.

Various formulations of FSH are available for clinical use. It is used commonly in infertility therapy to stimulate follicular development, notably in IVF therapy, as well as with interuterine insemination (IUI). FSH is available mixed with LH in the form of Pergonal or Menopur, and other more purified forms of urinary gonadotropins, as well as in a pure forms as recombinant FSH (Gonal F, Follistim), and as Follistim AQ, Gonal-F, Gonal-f RFF, Gonal-f RFF Pen.

Analogs of FSH are also clinically useful, which analogs include all biologically active mutant forms, e.g. where one, two, three or more amino acids are altered from the native form, PEGylated FSH, single chain bi-functional mutants, FSH-CTP, and the like. In an effort to enhance ovarian response several long-acting FSH therapies have been developed including an FSH-CTP (Corifollitropin alfa), where the FSH subunits are linked by the C-terminal peptide (CTP) moiety from human chorionic gonadotropin (hCG); and single-chain bi-functional VEGF-FSH-CTP (VFC) analog. FSH-CTP has a longer half-life in vivo, and may be administered, for example, with an interval of from one to four weeks between doses. See, for example, Lapolt et al. (1992) Endocrinology 131:2514-2520; and Devroey et al. (2004) The Journal of Clinical Endocrinology & Metabolism Vol. 89, No. 5 2062-2070, each herein specifically incorporated by reference.

LH and agonists. LH is a heterodimeric glycoprotein. Its structure is similar to that of the other glycoprotein hormones, follicle-stimulating hormone (FSH), thyroid-stimulating hormone (TSH), and human chorionic gonadotropin (hCG). The protein dimer contains 2 glycopeptidic subunits, labeled alpha and beta subunits, that are non-covalently associated. The alpha subunits of LH, FSH, TSH, and hCG are identical, and contain 92 amino acids in human but 96 amino acids in almost all other vertebrate species. The beta subunits vary. LH has a beta subunit of 120 amino acids (LHB) that confers its specific biologic action and is responsible for the specificity of the interaction with the LH receptor. This beta subunit if highly homologous to the beta subunit of hCG and both stimulate the same receptor.

LH is available mixed with FSH in the form of Pergonal, and other forms of urinary gonadotropins Recombinant LH is available as lutropin alfa (Luveris). All these medications are administered parenterally.

Often, hCG medication is used as an LH substitute because it activates the same receptor, is less costly, and has a longer half-life than LH. Human chorionic gonadotropin is a glycoprotein of 244 amino acids. The β-subunit of hCG gonadotropin contains 145 amino acids. Like other gonadotropins, hCG can be extracted from urine or by genetic modification. Pregnyl, Follutein, Profasi, Choragon and Novarel use the former method, derived from the urine of pregnant women. Ovidrel is a product of recombinant DNA. As an alternative, equine chorionic gonadotropin (eCG) is a gonadotropic hormone produced in the chorion of pregnant mares.

Candidates for Therapy. Any female human subject who possesses viable ovarian follicles is a candidate for therapy with the methods of the invention. Typically, the subject will suffer from some form of infertility, including premature ovarian failure. For instance, the subject may experience normal oocyte production but have an impediment to fertilization, as in, e.g. PCOS or PCOS-like ovaries. The methods of the invention may be especially useful in women who are not suitable candidates for traditional in vitro fertilization techniques involving an ovarian stimulation protocol. Included are patients with low responses to the conventional FSH treatment.

As described above, the methods of the invention are also useful in the treatment of infertility with various non-human animals, usually mammals, e.g. equines, canines, bovines, etc.

Premature ovarian failure (POF) occurs in 1% of women. The known causes for POF include genetic aberrations involving the X chromosome or autosomes as well as autoimmune ovarian damages. Presently, the only proven means for infertility treatment in POF patients involve assisted conception with donated oocytes. Although embryo cryopreservation, ovarian cryopreservation, and oocyte cryopreservation hold promise in cases where ovarian failure is foreseeable as in women undergoing cancer treatments, there are few other options. Due to heterogeneity of POF etiology, varying amounts of residual primordial follicle are still present in patients' ovaries for activation.

The degrees of ovarian follicle exhaustion vary among POF patients. The methods of the present invention allow the activation of the remaining primordial follicles in POF patients using PTEN inhibitors, followed by ovarian transplantation and R-spondin or CNP agonist treatment to promote the development of early follicles to the preovulatory stage. This may be followed by the retrieval of mature oocytes for IVF and subsequent pregnancy following embryo transfer. Due to the delay of child-bearing age in the modern society, many peri-menopausal women also are experiencing infertility as the result of diminishing ovarian reserve. Although gonadotropin treatments are widely used to promote the development of early antral follicles to the preovulatory stage, many peri-menopausal patients do not respond to the gonadotropin therapy. Because these women still have varying numbers of primordial follicles, they also benefit from the methods of the invention.

Methods of Enhancing Oocyte Maturation

Methods are provided for promoting the pre-antral development of mammalian ovarian follicles in vitro and in vivo, by contacting a preantral follicles with an effective dose of at least one of an R-spondin agonist or a CNP agonist, for a period of time sufficient to stimulate the development of a pre-antral to antral and preovulatory follicle.

Methods are also provided for pre-antral follicle stimulation, by contacting a pre-antral follicle with an effective dose of a CNP agonist, for a period of time sufficient to stimulate the development of a pre-antral follicle to an antral follicle. CNP is shown herein to promote the development of secondary/preantral follicles to the early antral stage, thus allowing efficient induction of ovulation by an LH agonist, e.g. by sequential eCG-hCG treatment. In some embodiments CNP can substitute for FSH in the penultimate stage of follicle development to the preovulatory stage, and as such CNP treatment could benefit patients with low responses to the conventional FSH treatment.

In some embodiments of the invention, the exposure is performed in vitro, e.g. in an organ or tissue culture, where at least one ovarian follicle is transiently exposed to an effective dose of at least one of an R-spondin agonist or a CNP agonist. The treated follicle may be utilized in vitro, for example for in vitro fertilization, generation of embryonic stem cells, etc., or may be transplanted to provide for in vivo uses. Transplantation modes of interest include, without limitation, transplantation of one or more follicles, including all or a fraction of an ovary, to a kidney capsule, to a subcutaneous site, to an ovarian site, e.g. where one ovary has been retained and one has been removed for ex vivo treatment, the one or more treated follicles may be transplated to the site of the remaining ovary.

In some embodiments, in vitro treatment is followed by ovarian transplantation to activate primordial or primary follicles for the generation of preovulatory oocytes, which may be followed by in vitro or in vivo fertilization.

Individuals of interest include endangered species, economically important animals, women suffering from premature ovarian failure, follicles derived from human embryonic stem cells and primordial germ cells, and the like. In other embodiments, the exposure is performed in vivo, locally, e.g. by intra-ovarian injection, or systemically administered to an individual.

Following exposure to an R-spondin or CNP agonist, the individual may be treated with follicular stimulating hormone (FSH) or FSH analogs, including recombinant FSH, naturally occurring FSH in an in vivo host animal, FSH analogs, e.g. FSH-CTP, pegylated FSH, and the like, at a concentration that is effective to initiate follicular growth.

Where the follicles have been stimulated to the antral stage, either with CNP, FSH, or agonists thereof, the individual may be treated lutenizing hormone (LH) or an agonist thereof, which agonists specifically include chorionic gonadotropins, e.g. equine chorionic gonadotropin (eCG), human chorionic gonatotropin (HCG), etc., at an ovulatory dose. In addition, the follicles may be exposed in vivo or in vitro to one or more of c-kit ligand, neurotrophins, vascular endothelial growth factor (VEGF), bone morphogenetic protein (BMP)-4, BMP7, leukemia inhibitory factor, basic FGF, keratinocyte growth factor; and the like.

The dose of R-spondin or CNP agonist is sufficient to stimulate pre-antral follicles to induce antral development as described above, and as such, will vary according to the specific agent that is used, the length of time it is provided in the culture, the condition of the follicles, etc. Methods known in the art for empirical determination of concentration may be used. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

As an example, follicle cultures may be contacted with one or both of a CNP agonist and an R-spondin agonist at the concentrations previously indicated, for a transient period of time of at least about 1 hour to about 24 hours, and may be from about 6 to about 12 hours. The concentrations may be adjusted to reflect the potency of other inhibitors.

Following release of follicles from dormancy, the oocytes present in the follicles may be utilized for in vitro purposes. In some embodiments the oocytes are utilized directly, and in others the follicles are contacted with one or more factors to modulate the oocyte maturation, e.g. the cultures may be contacted with a concentration of FSH or FSH analog sufficient to induce oocyte maturation in vitro, where the FSH or FSH analog may be recombinant, modified, native, etc. Alternatively CNP may be used to induce oocyte maturation. Following in vitro maturation the oocytes may be fertilized in vitro for implantation; may be fertilized in vitro for generation of stem cell lines; may be utilized without fertilization for various research purposes, and the like.

The follicles may be additionally cultured in the presence of one or more of c-kit ligand (Hutt et al., 2006; Parrott and Skinner, 1999), neurotrophins (Ojeda et al., 2000), vascular endothelial growth factor (Roberts et al., 2007), bone morphogenetic protein (BMP)-4 (Tanwar et al., 2008), BMP7 (Lee et al., 2001), leukemia inhibitory factor (Nilsson et al., 2002), basic FGF (Nilsson et al., 2001), keratinocyte growth factor (Kezele et al., 2005), and the like, where the factor(s) may be added in conjunction with one or both of a CNP agonist and an R-spondin agonist, or following exposure to one or both of a CNP agonist and an R-spondin agonist. For example, an LH agonist, including eCG and/or HCG may be administered following oocyte maturation by FSH or CNP.

In other embodiments the follicles may be transplanted to an animal recipient for maturation. As described above, methods are known in the art for transplantation of ovaries or fragments thereof at an ovarian site, at a kidney site, at a sub-cutaneous site, etc. are known in the art and may find use. Where the ovarian tissue is transplanted to an ovary, fertilization may proceed without additional in vitro manipulation. Where the ovarian tissue is transplanted to a non-ovarian site, e.g. a sub-cutaneous site, the oocytes may be subsequently removed for in vitro fertilization. The recipient may provide endogenous FSH for maturation of the oocytes, or may be provided with exogenous CNP or FSH or FSH analog for that purpose, including recombinant, long-acting FSH-CTP, and the like.

In other embodiments, the exposure is performed in vivo, locally or systemically administered to an individual. The data obtained from cell culture and/or animal studies can be used in formulating a range of dosages for humans. The dosage of the active ingredient typically lines within a range of circulating concentrations that include the $ED_{50}$ with little or no toxicity. The dosage can vary within this range depending upon the dosage form employed and the route of administration utilized. The individual is typically contacted with an effective concentration for at least about 6 hours, usually at least about 12 hours, and may be for at least about 1 day and not more than about one week, usually not more than about 3 days.

The compositions can also include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The one or both of a CNP agonist and an R-spondin agonist can be administered in a variety of different ways. Examples include administering a composition via oral, topical, intraperitoneal, intravenous, intramuscular, subcutaneous, subdermal, transdermal, intra-ovarian methods. In pharmaceutical dosage forms, the compounds may be administered in the form of their pharmaceutically acceptable salts, or they may also be used alone or in appropriate association, as well as in combination with other pharmaceutically active compounds.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Typical dosages for systemic administration range from 0.1 µg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

Following such exposure, the individual may be treated with CNP, or with recombinant FSH or FSH analogs, including, without limitation, naturally occurring FSH in an in vivo host animal, FSH analogs such as FSH-CTP, single chain analogs, pegylated FSH, and the like, at a concentration that is effective to release a mature oocyte. The individual may also be treated with an LH agonist as described above. Alternatively, the oocytes may be removed from the ovary and utilized for in vitro manipulation as described above.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Oocyte-derived R-spondin2 Promotes Ovarian Follicle Development

R-spondin proteins are adult stem cell factors capable of stimulating gut development by activating LGR4/5/6 receptors to activate the canonical Wnt signaling pathway. Although multiple Wnt ligands and cognate Frizzled receptors are expressed in the ovary, their physiological roles remain uncertain. Based on bioinformatics, RT-PCR, and in situ hybridization analyses, we demonstrated the expression of R-spondin2 in oocytes of follicles, from primary to preovulatory stages. Treatment of cultured somatic cells from preantral follicles with R-spondin2 and Wnt3a synergistically stimulated the canonical Wnt signaling pathway and cell proliferation. The stimulatory effects of R-spondin2 were blocked by Dickkopf1, an inhibitor of Wnt signaling. Although FSH also stimulated cell proliferation, it did not activate the canonical Wnt signaling pathway. In organ cultures of prepubertal ovaries containing small follicles, treatment with R-spondin2, similar to FSH, promoted the development of primary to secondary follicles. Basal and R-spondin2-stimulated follicle growth was blocked by DKK1 and by specific R-spondin2 antibodies. Furthermore, in vivo administration of a recombinant R-Spondin agonist stimulated the development of primary follicles to the secondary stage in both immature mice and GnRH antagonist-treated adult mice. Subsequent treatment with gonadotropins allowed the generation of mature oocytes capable of undergoing early embryonic development after in vitro fertilization. Thus, oocyte-derived R-spondin2 is a paracrine factor essential for early ovarian follicle development and R-spondin agonists provide a new treatment regimen for infertile women with low responses to the traditional gonadotropin therapy.

We demonstrate the exclusive expression of R-spondin2 in the oocyte of developing follicles and the ability of this oocyte factor to synergize with Wnt ligands in the stimulation of the canonical Wnt signaling pathway in ovarian somatic cells, leading to cell proliferation and follicle growth. After administration in vivo, an R-spondin agonist, like FSH, promoted the development of primary and secondary follicles to the antral stage. In addition to FSH, R-spondin2 represents another follicle stimulating factor.

Methods and Materials

Animals: Female ICR mice at different ages were obtained from Harlan Sprague-Dawley, Inc. (Indianapolis, Ind.) and housed at animal facility of Stanford University with 12 h dark/light and free access to food and water. The mice were treated in accordance with the guidelines of the local Animal Research Committee.

In situ hybridization analyses: To identify ovarian cell types expressing R-spondin2, in situ hybridization analysis were performed. Briefly, [$^{35}$S]-uridine triphosphate ($^{35}$S-UTP, PerkinElmer Inc, Waltham, Mass.)-labeled antisense and sense probes of mouse R-spondin2 cDNA (GenBank Accession No. BC156617.1, nucleotide 542-726) were generated using the Riboprobe In-Vitro Transcription Systems kit (Promega Corp.). Frozen sections of ovaries were cut at 8 μm and incubated with labeled probes (~5×10$^6$ cpm/ml) overnight at 56 C. After hybridization, slides were treated with RNAse A at 37 C for 30 min. to inactivate nonhybridized probes followed by washes in descending series of SSC buffer (2×SSC, 1×SSC, 0.5×SSC and 0.1×SSC) at 65 C for 30 min. before dehydration. To visualize the radiolabel, slides were dipped in photographic NTB-2 autoradiographic emulsion (Kodak, Rochester, N.Y.) and stored at 4 C for 10 days. D-19 developer and fixer (Kodak) were used to develop signals followed by hematoxylin counterstaining.

Real-time RT-PCR analyses and immunohistochemistry: Transcript levels for R-spondin2 and diverse Wnt and Frizzled genes in oocytes and somatic cells were analyzed together with those for different cell markers. Ovaries from day 10 mice were treated with 0.25% trypsin, 0.1% collagenase I, 0.02% DNaseI for 15 min. at 37 C. After adding 1 mM EDTA, ovaries were incubated at 37 C for 30 min. before collecting oocytes and remaining somatic cells. Total RNA was extracted using an RNeasy Micro Kit (QIAGEN Sciences, Valencia, Calif.) and cDNA was synthesized using a Sensiscript RT Kit (QIAGEN) according to the manufacture's protocol. Real-time PCR was performed using iTaq SYBR Green SuperMix (Bio-Rad Laboratories, Hercules, Calif.) on a Smart Cycler TD System (Cepheid, Sunnyvale, Calif.) as follows: 15 min. at 95 C and then 45 cycles of 15 sec. at 95 C and 60 sec. at 60 C. The relative abundance of specific genes was normalized to the relative abundance of β-actin levels.

Cell proliferation assay: Ovaries obtained from day 10 mice were digested with collagenase I, DNase, and trypsin. After centrifuging at 270×g for 10 min., cell pellet was washed and plated in a 96-well plate (BD Falcon, Franklin Lakes, N.J.) in McCoy's 5a medium (Gibco BRL, Grand Island, N.Y.) containing 4 mg/ml BSA (Sigma Aldrich Chemicals, St. Louis, Mo.), penicillin-streptomycin (Gibco) and sodium pyruvate (Gibco) for 3 h at 37 C. After washing twice with PBS to remove floating oocytes, cells were cultured in serum-free McCoy's 5a medium containing different factors for 48 h. MTS (3-(4,5-dimethylthiazol-2-yl)-5-(3-carboxymethoxyphenyl)-2-(4-sulfophenyl)-2H-tetrazolium) assay was performed using Cell Titer 96 Aqueous One Solution Cell Proliferation Assay (Promega, Madison, Wis.) by adding the substrate for 2 h before measuring absorbance at 490 nm.

TCF-luciferase assay: Ovarian somatic cells from day 10 mice were cultured overnight at 37 C in McCoy's 5a medium containing 10% fetal bovine serum (FBS; Gibco) before evaluation of Wnt signaling based on the TCF-luciferase assay. Cells were transfected with 1 μg of pTOP FLASH or pFOP FLASH plasmid together with 0.1 μg of pRL-TK plasmid using lipofectamine 2000 (Invitrogen, Carlsbad, Calif.) for 6 h. After culturing in McCoy's 5a medium containing 10% FBS overnight, cells were cultured in serum-free medium for 8 h and treated with R-spondin2, Wnt3a, and/or FSH for 18 h. Luciferase activity expressed as relative light unit was determined using a Dual Luciferase Reporter Assay Kit (Promega) with a luminometer (Bio-Rad).

Ovarian explant cultures: Ovaries from day 10 mice were placed on culture plate insert (Millipore, Bedford, Mass.) and cultured in 400 µl of DMEM/F12 (Gibco) containing 0.1% BSA (Sigma), 0.1% Albumax II (Gibco), insulin-transferrin-selenium (Gibco), 0.05 mg/ml L-ascorbic acid (Sigma) and penicillin-streptomycin (Gibco) under the membrane insert to cover ovaries with a thin layer of medium. Ovaries were treated with R-Spondin2 and/or FSH with media changes every 2 days for 4 days. For some groups, explants were also treated with DKK1 or R-Spondin2 antibodies (Santa Cruz Biotechnology, Santa Cruz, Calif.) to block R-spondin actions. Explants treated with non-immune IgG or boiled (100 C, 15 min) R-spondin2 antibodies served as negative controls. At the end of culture, ovaries were fixed in Bouin's solution, paraffin embedded, and cut into continuous sections before staining with hematoxylin and eosin. Only follicles with clearly stained oocyte nucleus were counted to prevent recounting of the same follicle.

In vivo treatment with R-spondin1-Fc, in vitro fertilization, and early embryo cultures: Mouse R-Spondin1-Fc fusion protein containing a C-terminal mouse antibody IgG2 Fc fragment was purified from the conditioned medium of stably transfected 293T cells using protein A affinity chromatography (20). Recombinant protein levels were determined by Coomassie blue staining and immunoblotting using R-spondin1 antibody (R&D systems). Wnt signaling activity was estimated based on the TCF luciferase assay in 293T cells. R-spondin1-Fc was injected intraperitoneally into day 10 mice (10 ug/day) daily for 5 days, followed by one injection of eCG (7 IU) and, at 48 h later, with an ovulatory dose (7 IU) of hCG. At 16 h later, the number of ovulated oocytes in the oviducts and the number of mature oocytes remaining in the ovary were determined. For studies in adult animals, mice at 9-10 weeks of age were pretreated i.p. with a GnRH antagonist (ORG37462, Schering-Plough, Inc., 1 ug/g BW) daily for 4 days, followed by treatment with R-spondin1-Fc (20 ug/day) together with the GnRH antagonist for 4 more days. Animals were then treated with a single injection of eCG (7 IU) and, at 48 h later, with hCG (7 IU). At 16 h later, the number of ovulated oocytes was determined. For in vitro fertilization, sperm from ICR male mice (10-12 weeks old) were collected into human tubal fluid media (Millipore) and incubated for 1 h at 37 C. Oocytes were fertilized with sperm ($2-3 \times 10^5$/ml) for 6 h and inseminated oocytes were transfer into KSOM-AA medium (Millipore) to allow development into blastocysts.

Results

Expression of R-spondin2 in oocytes of primary and larger follicles As shown in FIG. 1A, ovaries from neonatal mice at day 3 of age contained multiple primordial follicles at the ovarian cortex and some primary follicles migrated into the medulla region (FIG. 1Aa). Based on in situ hybridization analyses, positive R-spondin2 mRNA signals were only found in oocytes of primary follicles but not in cortical primordial follicles (FIG. 1Ab). In ovaries from juvenile mice at day 15 of age, follicles at primary, secondary and early antral stages were evident (FIG. 1Ac) and R-spondin2 signals were found in oocytes of primary and larger follicles (FIG. 1Ad). In ovaries of prepubertal mice (day 23 of age), the largest follicles reached the antral stage (FIG. 1Ae). Again, R-spondin2 expression was found in oocytes of primary and larger follicles (FIG. 1Af). No signals were found for sections with the sense probes.

Figure 1C:
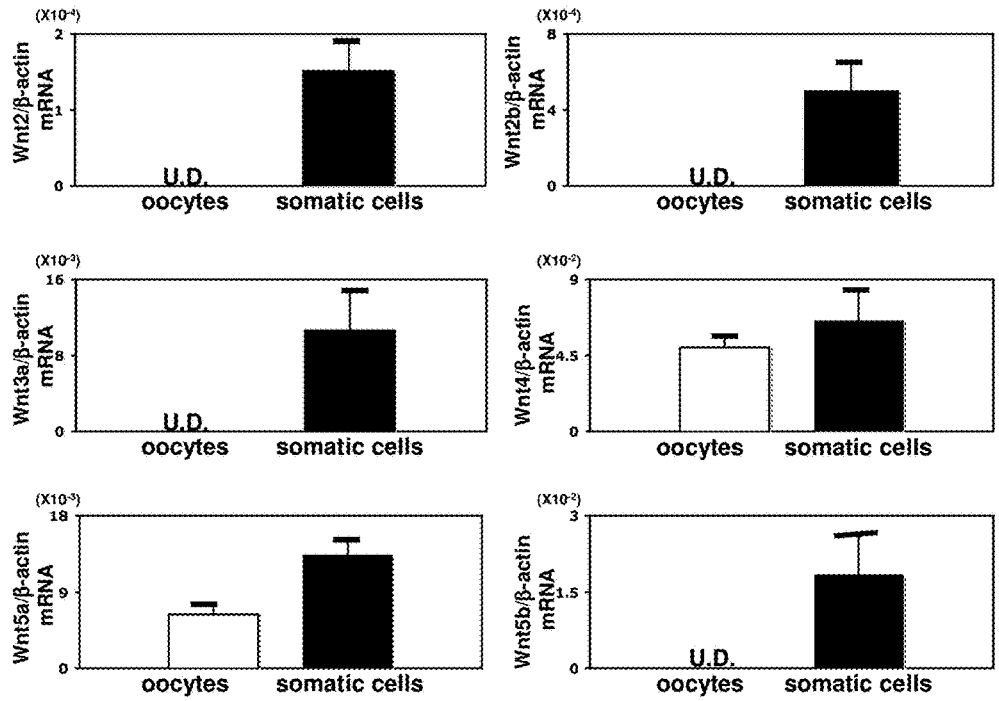
Figure 1D:
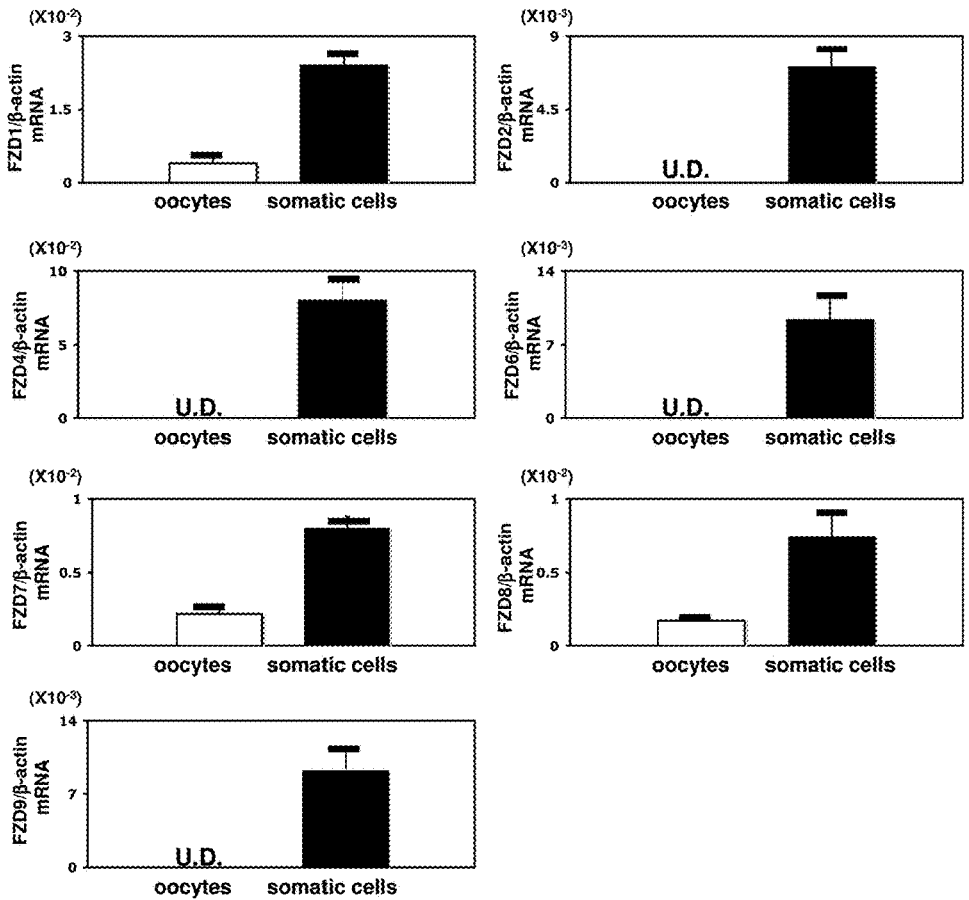

We performed real-time RT-PCR to investigate the expression levels of R-spondin2 together with diverse Wnt and Frizzled genes in oocyte and somatic cells obtained from ovaries of mice at day 10 of age. As shown in FIG. 1B, R-spondin2 was found in oocytes with minimal levels in somatic cells. GDF9, an oocyte marker, was only detected in oocytes whereas FSH receptor was found in somatic cells. As shown in FIG. 1C, transcripts levels for Wnt2, Wnt2b, Wnt3A, and Wnt5b were found in somatic cells but undetectable in oocytes. In contrast, transcripts for Wnt4 and Wnt5a were found in both somatic cells and oocytes. For Fizzled receptors (FIG. 1D), Frizzled2, Frizzled4, Frizzled6, and Frizzled9 transcripts were found only in somatic cells whereas Frizzled1, Frizzled7, and Frizzled8 were found in both oocytes and somatic cells with higher levels in the somatic cells.

Figure 2A:
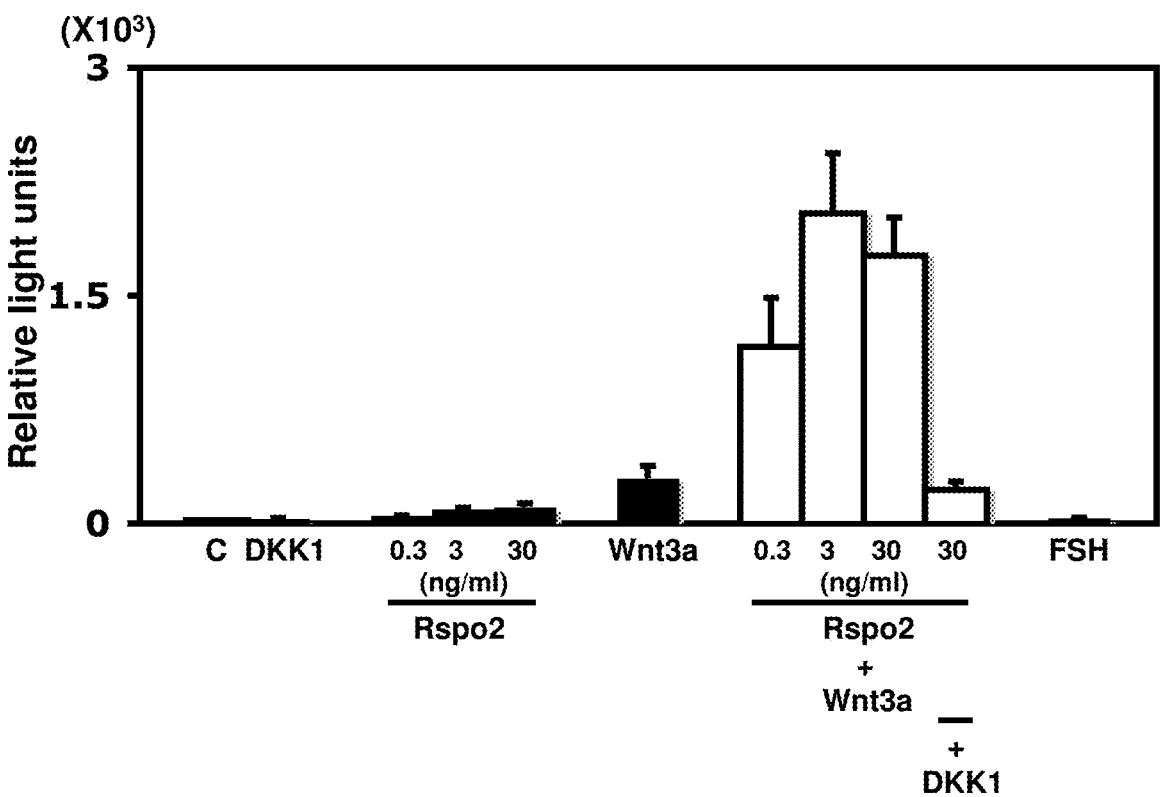
FIG. 2A-2B: Treatment with R-Spondin2 and Wnt3A stimulated the canonical Wnt signaling pathway and proliferation of somatic cells obtained from day 10 ovaries.
Figure 2B:
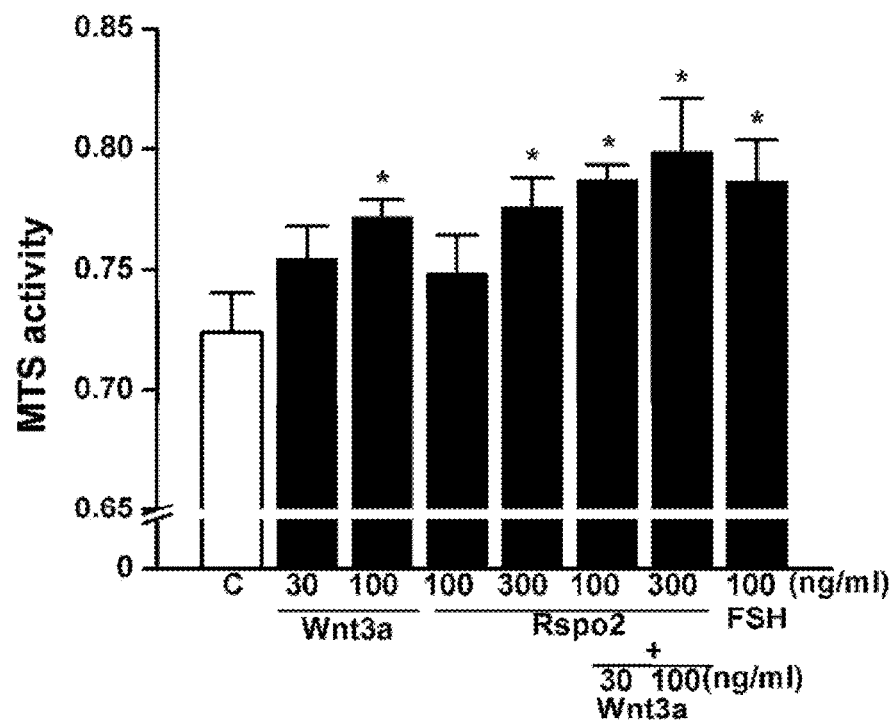

Treatment with R-spondin2 stimulated the canonical Wnt signaling pathway and proliferation of ovarian somatic cells To monitor the activation of the canonical Wnt signaling pathway, somatic cells were obtained from ovaries of day 10 mice and transfected with TCF-luciferase reporter plasmids before treatment with R-spondin2, Wnt3a, and/or FSH for 18 h. Luciferase activity was measured as an index of Wnt signaling. As shown in FIG. 2A, treatment with Wnt3a or R-spondin2 alone led to minimal stimulation of the TCF-luciferase activity whereas treatment with FSH was ineffective. In the presence of both Wnt3a and R-sponind2, synergistic increases in TCF-luciferase activity were evident. In addition, treatment with DKK1, an antagonist for Wnt signaling, blocked the stimulatory effects of R-spondin2 and Wnt3a. To estimate the number of viable cells, cells were also cultured with increasing doses of R-spondin2 with or without Wnt3a before measurement of mitochondrial reductase (MTS) activity. As shown in FIG. 2B, treatment with R-sponind2 or Wnt3a alone stimulated MTS activity in a dose-dependent manner. Treatment with both Wnt3a and R-Spondin2 led to further increases in MTS activity. Likewise, FSH treatment also increased the viable cell numbers.

R-spondin2 stimulated early follicle growth in organ explants Ovaries from day 10 mice were cultured with different factors for 4 days with media change at day 2 of culture. As shown in FIG. 3A, treatment with R-Spondin 2 increased ovarian weight in a dose-dependent manner with further increases found when both R-spondin2 and FSH were added together. Furthermore, co-treatment with the antagonist DKK1 inhibited basal and R-spondin2-stimulated ovarian weight gain. Morphological analyses suggested the promotion of ovarian follicle development following treatment with either R-spondin2 or FSH (FIG. 3C). The percentages of follicles at different developmental stages were evaluated by counting the number of follicles at each stage. Although negligible changes in the percentage of primordial and degenerated follicles were found, treatment with R-spondin2 and/or FSH decreased the ratio of primary follicles accompanied by increases in the percentage of secondary follicles (FIG. 3D), suggesting the promotion of early follicle development by R-sponind2 and FSH.

To investigate the roles of endogenous R-spondin2 secreted by oocytes on follicle growth, we incubated ovaries with specific R-spondin2 antibodies. As shown in FIG. 3E, treatment with affinity-purified R-spondin2 antibodies, but not non-immune IgG, suppressed basal and R-spondin2-stimulated ovarian weights. In addition, treatment with non-immune IgG or pre-boiled R-spondin2 antibodies did not affect ovarian weights, suggesting an important role of endogenous R-spondin2 in follicle growth.

In vivo treatment with R-spondin1-Fc promotes follicle development to allow gonadotropin stimulation of ovulation and early embryonic development We generated a chimeric R-spondin1-Fc protein by fusing the C-terminal end of human R-spondin1 cDNA with the Fc fragment of human IgG to facilitate secretion. After transfection of the expression plasmid in 293T cells, secreted R-spondin1-Fc protein was purified and tested for its ability to stimulate the Wnt signaling pathway. As shown in FIG. 4A, a single band of purified R-spondin1-Fc could be detected in immunoblots and treatment with increasing doses of Rspondin1-Fc, when added together with Wnt3a, stimulated TCF-luciferase activity in a dose-dependent manner. The potency of chimeric R-spondin1 is similar to that of recombinant human R-spondin2.

Prepubertal mice at day 10 of age were injected ip with R-spondin1-Fc (10 ug/day) daily for 5 days, followed by treatment with eCG for 48 h to stimulate the final stage of follicle maturation. As shown in FIG. 4B, increases in ovarian weight were found after R-spondin1-Fc treatment followed by eCG. Some of these animals were further treated with an ovulating dose (7 IU) of hCG before evaluating the number of ovulated eggs in oviducts at 16 h after hCG injection. To estimate the number of mature oocytes remaining in the ovary, mature oocytes were also recovered from ovaries using needle puncture. As shown in FIG. 5A, the number of ovulated and total mature eggs retrieved was higher in the R-spondin1-Fc-treated group as compared with the controls. These data demonstrated the ability of R-spondin1-Fc to promote the development of primary/secondary follicles, leading to the formation of preovulatory follicles capable of responding to gonadotropins to generate mature oocytes. To further demonstrate the stimulatory effects of the R-spondin agonist in adult mice, mice at 9-10 weeks of age were treated with a GnRH antagonist to reduce endogenous gonadotropin levels, followed by treatment with R-spondin1-Fc or saline for 4 days before treatment with eCG to induce the final stage of follicle maturation. Two days later, animals were injected with a single dose of hCG to induce ovulation. As shown in FIG. 5B, mature oocytes retrieved from oviducts and punctured out from ovaries were higher in R-spondin1-FC-treated animals as compared with controls. Subsequent in vitro fertilization and embryos cultures indicated a comparable percentage of oocytes obtained from control and R-spondin1-Fc-treated animals progressed to the blastocyst stage (FIG. 4C).

Our data indicated that R-spondin2 is an oocyte-expressed gene capable of promoting granulosa cell proliferation through the canonical Wnt signaling pathway. A strong synergism was found for oocyte-derived R-sponind2 and granulosa cell-derived Wnt ligands in the stimulation of the canonical beta-catenin pathway, leading to the promotion of early follicle development. These data underscores the important role of oocytes in controlling the fate of a given follicle. It is clear that the development of ovarian follicles is dependent on both gonadotropins produced by the anterior pituitary and local factors secreted by the oocyte.

The exclusive localization of R-spondin2 in the oocyte is supported by in situ hybridization and RT-PCR analyses. R-spondin2 transcripts are not found in primordial follicles but expressed in oocytes of primary and large follicles until the preovulatory stage. RT-PCR analyses further indicated negligible R-Spondin2 expression in somatic cells. Once the dormant follicles initiate growth, oocytes of growing follicle produce R-spondin2 to promote the proliferation of surrounding somatic cells. Consistent with our findings of multiple Wnt ligands and Frizzled receptors in somatic cells, earlier studies demonstrated the expression of Wnt2 and Frizzled4 in granulosa cells throughout follicle development. We also demonstrated the expression of LGR4 in ovarian granulosa cells, consistent with recent findings showing R-spondin proteins are ligands for LGR4, and earlier studies showing ovarian expression of LGR4.

Optimal activation of the canonical Wnt signaling in somatic cells requires synergistic stimulation by oocyte-derived R-spondin2 and somatic cell-derived Wnt proteins. The Wnt antagonist DKK1 prevents Wnt signaling by binding to the co-receptors LRP6 and Kremen1, leading to their internalization. Our findings of a suppressive effect of DKK1 in explants cultures indicated that promotion of follicle growth by R-spondin2 is mediated through the canonical Wnt pathway. Although FSH treatment in vivo also stimulates the development of preantral follicles, R-spondin and FSH likely act through independent pathways because FSH does not stimulate the TCF-luciferase reporter and the stimulatory effects of FSH on ovarian growth were not blocked by DKK1. The important role of Wnt signaling in ovarian somatic cell proliferation and follicle growth observed here is consistent with observed facilitation of FSH-induced follicular growth and suppression of follicle atresia found in transgenic mice over-expressing a dominant stable beta-catenin mutant in granulosa cells. Likewise, knockdown of WNT2 expression in rodent granulosa cells using transfected siRNA decreased DNA synthesis whereas WNT2 overexpression using a viral vector enhanced it. Neutralization of endogenous R-spondin2 using specific antibodies underscored the important role of endogenous oocyte-derived R-spondin2 in follicle development. Although multiple primordial follicles are initiated to start growth during each reproductive cycle, only few follicles developed to the preovulatory stage to release a mature oocyte. Because all follicles are under the influence of circulating FSH that could stimulate local Wnt expression, follicles with optimal R-spondin2 expression in their oocyte become dominant and successfully release a competent egg.

Although FSH treatment is widely used for infertility treatment, a subgroup of patients (FSH low-responders) showed minimal responses to gonadotropin treatment. These patients exhibit low antral follicle count and elevated serum FSH and AMH (anti-Mullerian hormone) levels at day 3 of their menstrual cycle. Although high doses of gonadotropins or adjuvant therapy with growth hormone or growth hormone releasing hormone have been used, minimal benefit is evident. Because the etiologies for FSH low responders are unclear and no rodent model for this clinical condition exists, we investigated the ability of R-spondin to promote follicle development in immature mice and adult mice treated with a GnRH antagonist to decrease endogenous gonadotropin levels. At day 10 of age in mice, most advanced follicles reached the secondary and preantral stage and exogenous administration with an R-spondin agonist promoted the progression of these follicles to the preovulatory stage. Following gonadotropin stimulation, more mature oocytes were generated. In adult mice treated with the GNRH antagonist, treatment with the R-spondin agonist also increased the number of mature oocytes capable of undergoing fertilization and embryonic development. Although R-spondin1 (100 μg/adult mice) treatments in vivo have been shown to stimulate intestinal stem cell proliferation and intestinal growth, we did not observe changes in intestinal length and PCNA staining under the present treatment protocol, likely due to the use of lower (5-fold) doses of the compound.

The present findings demonstrated the ability of R-spondin to promote the development of early follicles could serve as the basis for a new therapeutic approach by stimulating early stages of folliculogenesis.

Example 2

C-type Natriuretic Peptide Stimulates Ovarian Follicle Development

C-type natriuretic peptide (CNP) encoded by the NPPC gene expressed in ovarian granulosa cells inhibits oocyte maturation by activating the natriuretic peptide receptor-B (NPRB) in cumulus cells. RT-PCR analyses indicated increased NPPC and NPRB expression during ovarian development and follicle growth, associated with increases in ovarian CNP peptides in mice. In cultured somatic cells from infantile ovaries and granulosa cells from prepubertal animals, treatment with CNP stimulated cGMP production. Also, treatment of cultured preantral follicles with CNP stimulated follicle growth whereas treatment of ovarian explants from infantile mice with CNP, similar to FSH, increased ovarian weight gain. The stimulatory effects of both CNP and FSH were partially blocked by a protein kinase G inhibitor, consistent with observed stimulation of NPPC transcripts by FSH. In vivo studies further indicated that daily injection of infantile mice with CNP for four days promoted ovarian growth, allowing successful ovulation induction by gonadotropins. In prepubertal mice, CNP treatment also promoted early antral follicle growth to the preovulatory stage, leading to efficient ovulation induction by LH/hCG. Mature oocytes retrieved after CNP treatment could be fertilized in vitro and developed into blastocysts, allowing delivery of viable offspring. In xenografts of human ovarian cortical fragments, CNP treatments also stimulated follicle growth as revealed by follicle counting. Thus, CNP secreted by growing follicles is essential for preantral and antral follicle growth. In addition to FSH, treatment with CNP could provide a new therapy for female infertility.

Results

Expression of CNP and its receptor NPRB during follicle development: Real-time RT-PCR analyses indicated increased expression of NPPC and NPRB transcripts in somatic cells obtained from mice during prepubertal development (from day 7-19 of age) in an age-dependent manner with negligible levels in oocytes (FIGS. 5A and 5B). Granulosa cells and theca shells were also obtained from early antral follicles in prepubertal mice at day 23 of age and from preovulatory follicles in mice treated with eCG for two days. As shown in FIGS. 5A and B, the expression of both NPPC and NPRB transcripts was higher in granulosa cells than theca cells and oocytes. The purity of different cell types was confirmed using different cell markers (FIG. 5C, GDF9 for oocytes, FSH receptor for granulosa cells, and CYP17a1 for theca cells). We further isolated follicles of different sizes (90-140 um in diameters from mice at day 13 of age; 300-400 um in diameter from prepubertal mice; 500-600 um in diameter from eCG-treated mice). As shown in FIG. 5D, increases in both NPPC and NPRB transcript levels were detected during follicle development, reaching highest levels in preovulatory follicles (500-600 in diameters). To demonstrate the processing of mature CNP peptides from pro-CNP in the ovary, ovarian extracts from mice during prepubertal development were analyzed using specific EIA. As shown in FIG. 5E, ovarian CNP content increased in an age-dependent manner during the first wave of follicle development, reaching highest levels in animals at day 19 of age.

Stimulation of cGMP, but not cAMP, production by cultured ovarian somatic cells: Because the NPRB receptors mediated cGMP production stimulated by the CNP ligand, we isolated somatic cells from ovaries of mice at day 13 of age and granulosa cells from mice at day 21 of age before treatment with increasing doses of CNP or a high dose (30 nM) of ANP for 2 h. Media content of both cGMP and cAMP were determined by RIA. As shown in FIGS. 6A and B, treatment with CNP, but not ANP, led to dose-dependent increases in media content of cGMP for both cell preparations. In contrast, no changes in cAMP production after CNP treatment were detected for both types of cells.

CNP treatment promoted the growth of preantral follicles and cultured ovarian explants: Preantral follicles (125-135 um in diameter) were isolated from ovaries of mice at day 13 of age and treated with different hormones for four days with daily monitoring of follicle diameters. As shown in FIG. 7A, treatment with CNP led to dose- and time-dependent increases in follicle size, reaching levels comparable to those induced by a cGMP analog, 8-bromo-cGMP. In contrast, treatment with ANP was ineffective. Furthermore, combined treatment with CNP and FSH (25 ng/ml) led to additive increases in follicle growth (FIG. 7B). These findings demonstrated the ability of CNP to promote preantral follicle growth.

We further used ovarian explant cultures to investigate CNP actions. Individual ovaries from mice at day 10 of age were cultured for 4 days with CNP, ANP and/or FSH with media changes every two days. As shown in FIG. 8A, treatment with CNP, but not ANP, led to dose-dependent increases in ovarian weights. Similar to CNP, treatment with FSH also increased ovarian weights with additive increases when both CNP and FSH were included. Histological analyses indicated that treatment with CNP, like FSH, promoted the development of preantral follicles (FIG. 8B). Furthermore, treatment with Rp-8-Br-PET-cGMPs (Rp-cGMPS), a metabolically stable, competitive inhibitor of cGMP-dependent protein kinase G, blocked the stimulatory effects of CNP and partially suppressed the effects of a high dose of FSH. Because this inhibitor could partially block the stimulatory effects of FSH which is not capable of increasing cGMP production, we further tested if FSH treatment increased NPPC expression during ovarian culture. As shown in FIG. 8D, real-time RT-PCR analyses showed increases in NPPC transcript levels at both 2 and 4 days after FSH treatment, suggesting the stimulatory effects of FSH is partially mediated via stimulating CNP expression. In contrast, no changes in NPRB transcript levels were detected.

In vivo treatment with CNP promoted follicle development for ovulation and subsequent pregnancy in juvenile, prepubertal, and adult mice: To test the ability CNP to stimulate preantral follicle development in vivo, juvenile mice at day 13 of age were treated i.p. with CNP daily for 4 days. This was followed by a single i.p. injection of eCG for 2 more days before determination of ovarian weight. As shown in FIG. 9A, CNP treatment led a 56% increase in ovarian weight. Histological analyses indicated increases in the development of antral follicles after CNP treatment (FIG. 9B). Some of these animals were further treated with an ovulatory dose of hCG to check ovulation efficiency. As shown in FIG. 9C, higher numbers of ovulated oocyte were found in the oviducts of CNP-pretreated animals as compared with controls. These findings demonstrate the ability of ability of CNP to promote the development of secondary/ preantral follicles to the early antral stage, thus allowing efficient induction of ovulation by the sequential eCG-hCG treatment.

To further test the ability of CNP to stimulate the development of early antral follicles to the preovulatory stage, prepubertal mice at day 21 days of age were treated i.p. with CNP daily for 4 days followed by a single injection of an ovulatory dose of hCG. At 18 h after hCG treatment, the number of ovulated mature oocytes were determined. As shown in FIG. 10A, pretreatment with CNP increased ovarian weight. As compared with saline pretreated animals, CNP pretreatment led to an increase in the number of ovulated oocytes induced by hCG (FIG. 10B).

We further tested if ovulated oocytes retrieved after CNP pretreatment are capable of being fertilized. Oocytes were obtained from oviducts of CNP-pretreated prepubertal mice after hCG treatment and used for in vitro fertilization. We used oocytes obtained from prepubertal mice treated sequential with eCG (2 days) and hCG (16 h) as controls. As shown in FIG. 7, fertilized oocytes from CNP-pretreated animals developed to the blastocyst stage with the same efficiency as compared with control oocytes. Some prepubertal females pretreated with CNP followed by hCG to induce ovulation were mated with fertile males. Successful pregnancy was demonstrated followed by the delivery of healthy pups.

In addition to the role of CNP as an oocyte maturation inhibitor, our studies demonstrated the ability of CNP to promote preantral and antral follicle development. The NPPC gene is expressed in somatic/granulosa cells of preantral and antral follicles and exogenous CNP is capable of promoting follicle growth by stimulating cGMP production mediated through the NPRB receptor. Furthermore, the paracrine hormone CNP, acting through the cGMP pathway, likely mediates some of the effects of the endocrine hormone FSH in the promotion of preantral follicle development because FSH increased NPPC expression in ovarian explant cultures and part of the stimulatory effects of FSH on ovarian growth was blocked by an inhibitor for protein kinase G. Similar to the known follicle stimulating effects of FSH on preantral follicles in juvenile rats, CNP treatment of juvenile mice stimulated preantral follicle development to the early antral stage to allow penultimate stimulation by gonadotropins. Furthermore, CNP treatment of immature mice led to the formation of preovulatory follicles capable of responding to preovulatory LH/hCG stimulation, resulting in successful ovulation, fertilization, and pregnancy. These findings suggest that CNP can substitute for FSH in the penultimate stage of follicle development to the preovulatory stage.

CNP acts exclusively through the NPRB receptor to stimulate downstream cGMP signaling. Our findings are consistent with earlier studies using NPRB/GC-B null mice. In addition to the attenuation of longitudinal vertebra or limb-bone growth, female NPRB null mice were infertile and acyclic with smaller ovaries that contained only primordial through secondary follicles. Because CNP acts exclusively through the NPRB receptor, the arrest of follicle development at the secondary stage found in NPRB null mice underscores the essential role of CNP in the final stage of follicle development and the important role of CNP to mediate the actions of FSH.

Detection of NPPC transcripts and the CNP peptide in ovarian follicles at different stages of development in mice is consistent with an earlier study showing the presence of immunoreactive CNP in ovarian extracts during different phases of the estrous cycle in rats. Although we only investigated gene expression in punctured granulosa cells without cumulus cells, recent studies showed that cumulus cells express higher levels of NPRB receptors than mural granulosa cells and estradiol stimulation of NPRB expression. Our data further demonstrated increased expression of both NPPC and the NPRB receptor during follicle growth with preovulatory follicles expressing the highest levels of these genes. After the preovulatory LH surge, expression of NPPC and the ovarian content of CNP decreased in a time-dependent manner, concomitant with decreased levels of meiotic inhibitory activity associated with oocyte maturation. Coupled with our demonstration of the ability of CNP to promote follicle growth, CNP and its receptors in ovarian follicles are shown play important roles in both follicle somatic cell proliferation and the suppression of oocyte maturation during follicle development until the preovulatory LH surge. In patients, initiation of the preovulatory LH surge is also accompanied by decreased NPPC expression in granulosa cells and lower CNP secretion into the follicular fluid, coincident with cessation of follicle growth and resumption of meiotic maturation of oocytes.

Similar to the promoting effects of bromo-cGMP (a membrane-soluble cGMP analog) on the growth of cultured preantral follicles in rats, the present studies using cultured preantral follicles and ovarian explants demonstrated the ability of CNP to promote follicle development. In ovarian explant cultures, co-treatment with Rp-8-Br-PET-cGMPS (Rp-8Br-cGMP), a potent and selective inhibitor of cGMP-dependent protein kinase, blocked CNP actions. This finding is consistent with the ability of CNP to stimulate cGMP, but not cAMP, production by cultured somatic cells from ovaries of juvenile mice and cultured granulosa cells from early antral follicles. Thus, the follicle stimulating actions of CNP mediated by the cGMP pathway is distinct from the cAMP signaling pathway induced by FSH. In cultured ovarian explants containing preantral and smaller follicles, treatment with FSH increased the expression of NPPC but not NPRB transcripts. Also, the stimulatory effects of a high dose of FSH on ovarian explant growth were partially blocked by the cGMP-dependent protein kinase inhibitor. These data suggested that intraovarian CNP induced by FSH in preantral follicles could partially mediate the ovarian actions of FSH. Of interest, NPCC transcript levels also increased from antral follicles to preovulatory follicles but remained constant when expressed as per granulosa cells, reflecting stimulation of granulosa cell numbers. The exact cross-talks and overlapping actions of CNP-induced cGMP and FSH-stimulated cAMP pathways for ovarian follicle development require further analyses.

In vivo treatment using juvenile mice at day 13 of age demonstrated that CNP treatment promoted preantral follicle development and allowed subsequent eCG induction of preovulatory follicles capable of responding to an ovulatory surge of hCG, leading to ovulation. Furthermore, CNP treatment of prepubertal mice at day 21 of age facilitated the development of early antral follicles to the preovulatory stage, thus allowing the induction of ovulation by LH/hCG to generate fertilizable oocytes and successful pregnancy. Also, mature oocytes retrieved after CNP treatment have similar developmental potential comparable to those obtained after the conventional eCG-hCG sequential priming of immature mice. Because the NPRB receptor is expressed in granulosa cells but lower in theca cells and both granulosa and theca cells are required for optimal estrogen production by preovulatory follicles, in vivo treatment with CNP could stimulate granulosa cell functions and sufficient endogenous LH could promote theca cell functions to allow the stimulation of the final maturation of follicles to the preovulatory stage. Also, exogenous CNP could act through NPRB receptors expressed in theca cells. The ability of CNP, like FSH, to stimulate the development of preovulatory follicles in prepubertal mice also suggested that CNP could substitute for FSH in preovulatory follicle formation, underscoring the importance of CNP as a follicle-stimulating paracrine hormone, consistent with the reported follicle arrest at the secondary follicle stage found in NPRB null mice.

CNP acts exclusively through NPRB whereas ANP and BNP act through NPRA. Although CNP has been shown to have vasodilating, hypotensive, and natriuretic activities, we did not observe abnormalities following 4 days of CNP treatment using the present CNP dosages and injection protocols. The apparent lack of side effects using the present low doses of CNP is consistent with earlier reports showing minimal cardiac and renal actions using physiological concentrations of CNP. Indeed, short term infusion of CNP in humans, achieving supraphysiological levels in plasma, are not vasodepressor or natriuretic.

FSH treatment has been used extensively for the stimulation of follicle development to generate mature oocytes for fertilization. Our findings demonstrated that CNP could also stimulate both preantral and antral follicles, thus providing future opportunities for treatment of infertile women using this peptide hormone. CNP treatment could benefit patients with low responses to the conventional FSH treatment.

Methods and Materials:

Animals: Female CD1 mice at different ages were obtained from Charles River, Inc. (Indianapolis, Ind.) and housed at the animal facility of Stanford University with 12 h dark/light and free access to food and water. Mice were treated in accordance with the guidelines of the local Animal Research Committee.

Real-time RT-PCR analyses: Transcript levels for NPPC and NPRB in the ovary and different ovarian cell types were analyzed together with those for different cell markers. Ovaries from day 10 mice were treated with 0.25% trypsin, 0.1% collagenase I, 0.02% DNaseI for 15 min. at 37 C. After adding 1 mM EDTA, ovaries were incubated at 37 C for 30 min. before collecting oocytes and remaining somatic cells. In addition, early antral follicles were isolated from prepubertal mice at day 23 of age and punctured to collect granulosa cells and oocytes, and for obtaining theca shells. Similar procedures were used to isolate granulosa cell, oocytes, and theca shell from preovulatory follicles at 48 h after treatment of prepubertal mice with eCG (5 IU). Total RNA was extracted using an RNeasy Micro Kit (QIAGEN Sciences, Valencia, Calif.) and cDNA was synthesized using a Sensicript RT Kit (QIAGEN) according to the manufacture's protocol. Real-time PCR was performed using iTaq SYBR Green SuperMix (Bio-Rad Laboratories, Hercules, Calif.) on a Smart Cycler TD System (Cepheid, Sunnyvale, Calif.) as follows: 15 min. at 95 C and then 45 cycles of 15 sec. at 95 C and 60 sec. at 60 C. Data were analyzed by the cycle threshold method to determine the fold changes in expression. The relative abundance of specific genes was normalized to the relative abundance of beta-actin levels.

Measurement of ovarian CNP levels: For EIA measurement of CNP peptide levels, ovaries from mice at different ages were obtained and boiled for 5 min. in 5 volumes of water to inactivate intrinsic proteases. The solution was then adjusted to 1M AcOH and 20 mM HCl. Ovaries were homogenized with a Polytron mixer (VWR International, West Chester, Pa.) before centrifugation at 20,000×g for 30 min. at 4 C. The supernatant of extracts was subjected to precipitation at a concentration of 66% acetone. After removing the precipitates by centrifugation for 30 min. at 3,000×g, acetone in the supernatant was evaporated and extracted peptides dissolved in water before EIA analyses using a CNP EIA kit (Phoenix Pharmaceuticals, Inc., Burlingame, Calif.) according to manufacturers instructions.

Dissection follicles of different sizes and culturing of preantral follicles: For RT-PCR analyses, early secondary follicles of 90-140 um in diameters were isolated from mice at day 13 of age whereas antral follicles (300-400 um in diameter) were isolated from prepubertal mice at day 23 of age. Preovulatory follicles (500-600 um in diameter) were isolated from prepubertal mice treated with eCG (5 IU). For follicle cultures, preantral follicles (125-145 um in diameter) were isolated from mice at day 13 of age and cultured individually in 96 well plates containing alpha-MEM (100 ul/well) with penicillin and streptomycin together with insulin, transferrin and selenium. Explants were treated with or without CNP, ANP, 8-bromo-cGMP, and/or FSH. The media were changed every two days and follicle growth was monitored daily by measuring follicle diameters.

Ovarian explant cultures: Ovaries from day 10 mice were placed on culture plate inserts (Millipore, Bedford, Mass.) and cultured in 400 μl of DMEM/F12 containing 0.1% BSA (Sigma), 0.1% Albumax II, insulin-transferrin-selenium, 0.05 mg/ml L-ascorbic acid and penicillin-streptomycin under the membrane insert to cover ovaries with a thin layer of medium. Ovaries were treated with CNP and/or FSH with media changes every 2 days for 4 days. Some explants were also treated with a pan-specific protein kinase G inhibitor, Rp-8-Br-PET-cGMPS (BioLog, Bremen, Germany). At the end of culture, ovaries were fixed in Bouin's solution, paraffin embedded, and cut into continuous sections before staining with hematoxylin and eosin.

In vivo treatment with CNP, ovulation, and pregnancy: Infantile mice at day 13 of age were treated with CNP (20 ug/kg body weight) i.p. daily for 4 days. This was followed by a single injection of eCG (5 IU) for 2 days to stimulate penultimate follicle maturation before collection of ovaries for weighting and histological analyses. Some animals were further treated with an ovulatory dose (5 IU) of hCG and oocytes in oviducts were monitored at 16 h later to evaluate ovulation efficiency. To test the effects of CNP on early antral follicle growth, prepubertal mice at day 21 of age were treated intraperitoneally with CNP (50 ug/kg body weight) daily for four days to stimulate preovulatory follicle development, followed by the injection of an ovulatory dose (2.5 IU) of hCG. At 16 h later, number of ovulated oocytes was determined. Mature oocytes obtained from CNP-pretreated animals were used for in vitro fertilization. Sperm from CD1 male mice (10-12 weeks old) were collected into human tubal fluid media (Millipore) and incubated for 1 h at 37 C. Oocytes were fertilized with sperm ($2-3 \times 10^5$/ml) for 6 h and inseminated oocytes were transfer into KSOM-AA medium (Millipore) to allow development into blastocysts. Some of the CNP-pretreated females were mated with fertile males for the monitoring of pregnancy and the delivery of pups.

Statistical analyses: Results are presented as mean±SE of three or more independent determination. Statistical significance was determined by using the ANOVA test followed by Fisher's protected least significant difference with $P<0.05$ being statistically significant.

The abbreviations used are: CNP, C-type natriuretic peptide; ANP: atrial natriuretic peptide; BNP, brain natriuretic peptide, eCG, equine chorionic gonadotropin; hCG: human chorionic gonadotropin; NPRB, natriuretic peptide receptor-B; NPRA, natriuretic peptide receptor-A; EIA: enzyme-linked immunoassay; RIA, radioimmunoassay.

All publications and patent applications cited in this specification are herein incorporated by reference as if each individual publication or patent application were specifically and individually indicated to be incorporated by reference. The publications discussed herein are provided solely for their disclosure prior to the filing date of the present application. Nothing herein is to be construed as an admission that the invention is not entitled to antedate such a disclosure by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of stimulating the development of a human pre-antral follicle to an antral follicle, the method comprising:
    transiently contacting at least one human ovarian pre-antral follicle in vitro with an effective dose of one or both of C-type natriuretic peptide (CNP) or a CNP fusion protein; and R-spondin 1 protein, R-spondin 2 protein, R-spondin 1 fusion protein, or R-spondin 2 fusion protein, in a dose effective to stimulate the human pre-antral ovarian follicle for a period of from one hour to five days to promote development to an antral follicle.

2. The method of claim 1, further comprising harvesting the antral follicle.

3. The method of claim 2, further comprising transplantation of the antral follicles to a human in in vivo recipient.

4. The method of claim 3, further comprising administering an LH agonist to said recipient following implantation.

5. The method of claim 4, where the recipient is autologous to the ovarian follicle.

* * * * *

UNITED STATES PATENT AND TRADEMARK OFFICE
CERTIFICATE OF CORRECTION

PATENT NO. : 10,792,311 B2  
APPLICATION NO. : 15/978947  
DATED : October 6, 2020  
INVENTOR(S) : Yuan Cheng et al.

Page 1 of 1

It is certified that error appears in the above-identified patent and that said Letters Patent is hereby corrected as shown below:

In the Specification

At Column 1, immediately after Line 13, before Line 15, it should read:
-- FEDERALLY SPONSORED RESEARCH AND DEVELOPMENT
This invention was made with government support under grant HD0608158 awarded by the National Institutes of Health. The government has certain rights in the invention. --

Signed and Sealed this  
Seventeenth Day of November, 2020

Andrei Iancu  
*Director of the United States Patent and Trademark Office*